(12) United States Patent
Laguerre et al.

(10) Patent No.: US 11,786,839 B2
(45) Date of Patent: Oct. 17, 2023

(54) EUTECTIC EXTRACT FORMATION AND PURIFICATION

(71) Applicants: Givaudan France Naturals SAS, Avignon (FR); Scionix, London (GB)

(72) Inventors: Michaël Laguerre, Le Pontet (FR); Robert Harris, Leicester (GB); Alexis Lavaud, Sierentz (FR); Mathieu Tenon, Malemort du Comtat (FR); Simona Birtic, Cavaillon (FR); Antoine Charles Bily, Vedène (FR); Andrew Peter Abbott, Leicester (GB)

(*) Notice: Subject to any disclaimer, the term of this patent is extended or adjusted under 35 U.S.C. 154(b) by 148 days.

(21) Appl. No.: 17/055,822

(22) PCT Filed: May 15, 2019

(86) PCT No.: PCT/EP2019/062535
§ 371 (c)(1),
(2) Date: Nov. 16, 2020

(87) PCT Pub. No.: WO2019/219774
PCT Pub. Date: Nov. 21, 2019

(65) Prior Publication Data
US 2021/0299592 A1 Sep. 30, 2021

(30) Foreign Application Priority Data
May 16, 2018 (GB) ..................................... 1807968

(51) Int. Cl.

| | |
|---|---|
| *A61K 8/41* | (2006.01) |
| *A61K 8/49* | (2006.01) |
| *A61K 8/97* | (2017.01) |
| *A61K 36/23* | (2006.01) |
| *A61K 36/28* | (2006.01) |
| *A61K 36/45* | (2006.01) |
| *A61K 36/53* | (2006.01) |
| *A61K 36/725* | (2006.01) |
| *A61K 36/752* | (2006.01) |
| *A61K 36/81* | (2006.01) |
| *A61Q 19/00* | (2006.01) |
| *B01D 11/02* | (2006.01) |

(52) U.S. Cl.
CPC .......... *B01D 11/0288* (2013.01); *A61K 8/416* (2013.01); *A61K 8/4926* (2013.01); *A61K 8/4946* (2013.01); *A61K 8/97* (2013.01); *A61K 36/23* (2013.01); *A61K 36/28* (2013.01); *A61K 36/45* (2013.01); *A61K 36/53* (2013.01); *A61K 36/725* (2013.01); *A61K 36/752* (2013.01); *A61K 36/81* (2013.01); *A61Q 19/00* (2013.01); *A61K 2236/30* (2013.01)

(58) Field of Classification Search
None
See application file for complete search history.

(56) References Cited

FOREIGN PATENT DOCUMENTS

| CN | 107759556 A | 3/2018 |
|---|---|---|
| WO | 2016162703 A1 | 10/2016 |

OTHER PUBLICATIONS

Mariana Ruesgas-Ramon et al. ("Application of Deep Eutectic Solvents (DES) for Phenolic Compounds Extraction: Overview, Challenges, and Opportunities", Journal of Agricultural and Food Chemistry, vol. 65, No. 18, May 10, 2017 (May 10, 2017), pp. 3591-3601.) within the IDS (Year: 2017).*
Great Britain Search Report for Application No. 1807968.1 dated Dec. 27, 2018.
International Search Report for Application No. PCT/EP2019/062535 dated Dec. 5, 2019.
International Written Opinion for Application No. PCT/EP2019/062535 dated Dec. 5, 2019.
Bernardo Dis Ribiero, et al., Extraction of saponins from sisal (*Agave sisalana*) and jua (*Ziziphus joazeiro*) with cholinium-based ionic liquids and deep eutectic solvents, European Food Research and Technology, 2013, pp. 965-975, vol. 237, Springer.
Sylwia Bajkacz, et al., Development of a Method Based on Natural Deep Eutectic Solvents for Extraction of Flavonoids from Food Samples, Food Analytical Methods, Dec. 2, 2017, pp. 1330-1344, vol. 11, Springer.
Mariana Ruesgas-Ramon, et al., Application of Deep Eutectic Solvents (DES) for Phenolic Compounds Extraction: Overview, Challenges, and Opportunities, Journal of Agricultural and Food Chemistry, Apr. 17, 2017, pp. 3591-3601, vol. 65, ACS Publications, American Chemical Society.
Weiyang Tang, et al., Optimal separation of phenol from model oils by forming deep eutectic solvents with quaternary ammonium salts, Korean Journal of Chemical Engineering, Mar. 2017, pp. 814-821, vol. 34, Issue 3.

\* cited by examiner

*Primary Examiner* — Michael Barker
*Assistant Examiner* — Randall O Winston
(74) *Attorney, Agent, or Firm* — Curatolo Sidoti & Trillis Co., LPA; Salvatore A. Sidoti; Floyd Trillis, III

(57) ABSTRACT

The present invention relates to processes for forming eutectic extracts, processes for purifying eutectic extracts and uses of the eutectic extracts such as in food-stuffs, pharmaceuticals, nutraceuticals and supplements, such as food supplements and sports supplements.

7 Claims, 7 Drawing Sheets

EUTECTIC EXTRACT FORMATION AND PURIFICATION

The present invention relates to processes for forming eutectic extracts, processes for purifying eutectic extracts and uses of the eutectic extracts such as in aroma and fragrances, food-stuffs, cosmetic products, pharmaceuticals, nutraceuticals and supplements, such as food supplements and sports supplements.

The extraction of molecules from natural products is a common process which is usually carried out using water or volatile organic solvents.

The extract profile is generally controlled by the polarity of the solvent and the temperature of the extraction. While approximately 300 molecular solvents exist, only a small range are used for natural product extraction due to possible toxicity concerns and unwanted solvent characteristics, such as the boiling point of the solvent.

Typically, extracts that are to be used for human consumption are obtained using alcoholic based solvent or supercritical fluids (usually $CO_2$) due to their lack of toxicity.

Some studies have been carried out using deep eutectic solvents (DES) as extraction solvents (Abbott A P, Capper G, Davies D L, Rasheed R K, Tambyrajah V. Novel solvent properties of choline chloride/urea mixtures. Chem. Commun. 2003, 7, 70-71; Choi Y H, van Spronsen J, Dai Y, Verberne M, Hollmann F, Arends IWCE, Witkamp G J, Verpoorte R. Are natural deep eutectic solvents the missing link in understanding cellular metabolism and physiology, Plant Physiol. 2011, 156, 1701-1705) and have resulted in the industrialization and the commercialization of extracts obtained using these solvents (Laguerre M, Lavaud A. The rise of deep eutectics from nature to cosmetics. Personal Care 2016, 45-47).

However, apart from chromatographic methods which are typically time consuming and low yielding, there are no methods available to separate the "actives" present in the deep eutectic solvent. This is mainly due to the low volatility of DES that makes it difficult to remove from the extract by evaporation.

Consequently, the resulting liquid extracts obtained using DES have the major drawback that they are extremely diluted with the solvent, with limited methods of concentrating them further using current cost-effective purification techniques.

This limitation has had a significant impact on the commercial values for different markets.

At the present time, there is no process for extracting, from a biological material, active ingredients or substances such as phenolic compounds, antioxidants, saponins, carotenoids, terpenes or others, using deep eutectic solvents (whether or not they are constituted from naturally-occurring components), whilst ensuring that the resulting extracts contain high levels of active compounds. There is also no process for concentrating eutectic extracts in such a way that the active compound level and activity of the extract is increased.

The listing or discussion of an apparently prior-published document in this specification should not necessarily be taken as an acknowledgement that the document is part of the state of the art or common general knowledge.

DISCLOSURE OF THE INVENTION

Extraction Process

The present inventors have surprisingly and unexpectedly found that eutectic extracts can be obtained in-situ by mixing at least one exogenous amine with a plant and/or animal and/or prokaryotic biological material.

The present invention provides a process for preparing a liquid, gel or gel-like eutectic extract comprising the steps of:
(i) forming a mixture between
(a) at least one exogenous amine; and
(b) biological material which is plant and/or animal and/or prokaryotic biological material;
(ii) allowing the mixture to interact to form a liquid, gel or a gel-like eutectic extract;
(iii) optionally, separating the liquid, gel or gel-like mixture from undissolved solids.

This process is hereinafter referred to as the extraction process of the invention.

As used herein, the term "eutectic" means a homogeneous mixture of substances that melts or solidifies at a single temperature that is lower than the melting point of the constituents of the mixture.

As used herein, the term "deep eutectic" means systems/mixtures formed from a eutectic mixture of Lewis or Brønsted acids and bases which can contain a variety of anionic and/or cationic species.

As used herein, the term "plant biological material" is material that has been obtained from or is obtainable from plants, such as from roots, aerial parts, leaves, flowers, stems, barks, fruits or seeds or their tissues.

As used herein, the term "animal biological material" is material that has been obtained from or is obtainable from an animal source, such as from secretions from the glands of mammals, i.e. musk.

As used herein, the term "prokaryotic biological material" is material that has been obtained from or is obtainable from single cell organisms, such as bacteria.

As will be appreciated by the person skilled in the art, as used herein the term "obtainable from" means that the plant and/or animal and/or prokaryotic biological material may be obtained from a plant/animal/prokaryote directly or may be isolated from the plant/animal/prokaryote, or may be obtained from an alternative source, for example by chemical synthesis or enzymatic production. Whereas the term "obtained" as used herein, means that the extract is directly derived from the plant/animal/prokaryote source.

The eutectic extract obtained or obtainable from the process of the invention (hereinafter referred to as the eutectic extract of the invention) may be in the form of a liquid or a gel/gel-like. In certain aspects, the extract is in the form of a liquid. In other aspects, the extract is in the form of a gel or is gel-like. For example, the eutectic extract obtained or obtainable from the process of the invention may have a viscosity from about 1 cP at 20° C. to about 100,000 cP at 20° C.

As used herein, the term "liquid" means a state of matter in which atoms or molecules within the liquid can more freely, while remaining in contact with one another, and will take the shape of its container. Typically, a liquid will have a viscosity from about 1 cP at 20° C. to about 10,000 cP at 20° C., such as from about 50 cP at 20° C. to about 5,000 cP at 20° C.

As used herein, the term "gel" or "gel-like" means a state of matter where the atoms or molecules are in a rigid or semi-rigid mixture, which typically exhibits little to no flow when in the steady-state. Typically, a gel or gel-like substance will have a viscosity from about 10,000 cP at 20° C.

to about 250,000 cP at 20° C., such as from about 30,000 cP at 20° C. to about 100,000 cP at 20° C.

The eutectic extract of the invention may comprise any natural compounds endowed with properties that are of cosmetic or nutritional interest such as natural biological flavourings and taste modifiers, fragrances, biocides, antimicrobials, proteins, enzymes, colourings, pigments, surfactants, chelatants, antioxidants, vitamins and mixtures thereof from the plant and/or animal and/or prokaryotic biological material.

Typically, the natural compounds endowed with properties that are of cosmetic or nutritional interest such as natural biological flavourings and taste modifiers, fragrances, biocides, antimicrobials, proteins, enzymes, colourings, pigments, surfactants, chelatants, antioxidants, vitamins and mixtures thereof are present in the eutectic extract as phenolic compounds (including phenolic acids, phenolic esters, phenolic diterpenes, flavonoids, secoiridoids, stilbenes and phenolic alcohols), essential oils, terpenoids (including mono-, sesqui-, di-, tri-, and tetra-terpenoids such as carotenoids), alkaloids, lipids, phenylpropanoids, and mixtures thereof, from the plant and/or animal and/or prokaryotic biological material.

Step (i)

Step (i) of the process may be conducted in the absence of added organic solvents.

Step (i) of the process may be conducted in the absence of additional hydrogen bond forming compounds, other than the at least one exogenous amine or water. For example, Step (i) of the process may be as follows:
(i) forming a mixture between
  (a) at least one exogenous amine;
  (b) biological material which is plant and/or animal and/or prokaryotic biological; and
  (c) water.

Typically, the at least one exogenous amine as used in the process is not a constituent of a eutectic or deep eutectic solvent or mixture.

The water may be directly added to the at least one exogenous amine and biological material, may be adsorbed by the least one exogenous amine and biological material while the mixture is being formed or may be present as endogenous water in the biological material.

Without wishing to be bound by theory, it is thought that the addition of water accelerates the process by aiding mass transport. Typically, in step (i) of the process, water may be present in an amount from about 0 to about 70% by weight of the mixture, such as from about 5 to about 60% by weight or from about 10 to about 30% by weight.

In step (i) of the process a pre-formed eutectic solvent is not added to the biological material. The eutectic solvent is instead formed in-situ with the biological material.

As used herein, the term "exogenous amine" means that the amine is not already present in the plant and/or animal and/or prokaryotic biological material and must be added to the plant and/or animal and/or prokaryotic biological material.

The at least one exogenous amine may be selected from the group consisting of quaternary ammoniums, pyridinium amines, alkylimidazolium amines and mixtures thereof. For example, the at least one exogenous amine may be selected from the group consisting of choline chloride (ChCl), benzyltriethyl ammonium chloride (BTEAC), benzyltrimethyl ammonium chloride (BTMAC), carnitine, betaine and 1-butyl-3-methylimidazolium chloride (BminCl) and mixtures thereof.

The at least one exogenous amine may be in the form of a solid, such as a powder, or the amine could be in the form of an aqueous solution.

The biological material is preferably plant biological material. The plant biological material may be obtained from or obtainable from plant roots, aerial parts, leaves, flowers, stems, barks, fruits or seeds or their tissues. For example, the fruit tissue may be the rind of the fruit.

The plant biological material may be obtained from or obtainable from Lamiaceae (including rosemary, *Salvia*, or any other species from the Lamiaceae family), *Citrus*, tree barks (such as *Cedrus* bark), *Choisya* (such as *Choisya× dewitteana* 'Aztec Pearl' (*Choisya ternate*)), Blueberry (*Cyanococcus*) (such as dried Blueberry), *Capsicum* (*Capsicum annuum*), Green chilli (*Capsicum frutescens*), Aubergine (*Solanum melongena*) (such as dried Aubergine), Ginger (*Zingiber officinale*), Cilantro, *Ziziphus, silybum* (such as *silybum marianum*) and *Orthosiphon*.

The biological material comprises at least one endogenous compound capable of forming a complex with the at least one exogenous amine. The complex formed between the at least one endogenous compound in the biological material and the at least one exogenous amine may be formed via hydrogen bonds and/or ion-dipole interactions.

As used herein, the term "endogenous compound" means that the compound is already present in the plant and/or animal and/or prokaryotic biological material and is not added to the plant and/or animal and/or prokaryotic biological material.

The at least one endogenous compound may be selected from the group consisting of amino acids, peptides, proteins, carbohydrates, fatty acids, triacylglycerols or other lipids, vitamins, organic acids, polyols, enols, alkaloids, secoiridoids, terpenoids, phenolic compounds and mixtures thereof.

Step (i) of the process is typically conducted using a mass ratio of amine:plant and/or animal and/or prokaryotic biological material of from about 1:1 to about 10:1, such as from about 2:1 to about 8:1 or from about 4:1 to about 6:1.

In step (i) of the process the biological material may be selected from the groups consisting of rosemary, such as rosemary leaf, *Choisya*, such as *Choisya ternate*, blueberry, such as dried blueberry juice, *Capsicum*, aubergine, such as dried aubergine (with or without the skin), ginger, *cedrus* bark, *Orthosiphon, Ziziphus*, cilantro, *silybum marianum* (milk thistle), *Salvia officinalis* and mixtures thereof; and the at least one exogenous amine may be selected from ChCl, BTEAC, BTMAC, carnitine, betaine, BmimCl and mixtures thereof, in a ratio of amine to biological material of from about 1:1 to about 10:1, such as from about 2:1, 3:1, 4:1, 5:1, 6:1, 7:1, 8:1 or 9:1 to about 9:1, 8:1, 7:1, 6:1, 5:1, 4:1, 3:1 or 2:1.

In step (i), the plant and/or animal and/or prokaryotic biological material mixed with the at least one exogenous amine may be in solid, liquid, gel or gel-like form. For example, the biological material may be in solid form as a powder.

The plant and/or animal and/or prokaryotic biological material may be in the form of a liquid, such as fluid from the biological material, i.e. juice from a plant or fruit.

Alternatively, the biological material may be in the form of a solid, such as ground or mashed biological material, i.e. ground or mashed material obtained or obtainable from plant roots, aerial parts, leaves, flowers, stems, barks, fruits or seeds or their tissues.

If the plant and/or animal and/or prokaryotic biological material mixed with the at least one exogenous amine is in the form of a liquid (i.e. juice), the liquid biological material may be mixed with the at least one exogenous amine in step (i) and the resulting mixture dried.

Alternatively, the liquid plant and/or animal and/or prokaryotic biological material may be dried before being mixed with the at least one exogenous amine in step (i).

Any suitable drying techniques known in the art may be used, such as, but not limited to, freeze-, spray-, oven-, heat- or vacuum-drying.

If required, the dried liquid plant and/or animal and/or prokaryotic biological material may be ground into a powder before being mixed with the at least one exogenous amine in step (i).

If the plant and/or animal and/or prokaryotic biological material mixed with the at least one exogenous amine in step (i) is a solid, the solid plant and/or animal and/or prokaryotic biological material may be obtained by drying the plant and/or animal and/or prokaryotic biological material to remove excess water, such as by freeze drying or heat drying.

The dried biological material may then be ground into a powder.

Alternatively, the solid plant and/or animal and/or prokaryotic biological material may be used fresh without the removal of endogenous water present.

Step (ii)

Once the at least one exogenous amine has been mixed with the plant and/or animal and/or prokaryotic biological material, the mixture is allowed to interact in step (ii) and may be subjected to heat and/or mechanical action.

It is through the direct addition of the at least one exogenous amine to the plant and/or animal and/or prokaryotic biological material, a deep eutectic mixture is formed in-situ in step (ii).

Step (ii) may be conducted at a temperature from about 0 to 120° C., such as from about 10 to about 100° C.

If mechanical action is used in step (ii), this may be provided by using a pestle and mortar, extruder, ball mill or other means by which mechanical pressure can be applied known to the skilled person.

The at least one exogenous amine and plant and/or animal and/or prokaryotic biological material may interact in step (ii) from about 30 minutes to about 20 days, for example from about 1 hour to about 15 days, or about 10 days.

Step (ii) allows for the formation of a complex between the at least one exogenous amine and the endogenous compounds present in the plant and/or animal and/or prokaryotic biological material. The complex may be formed via hydrogen bonds and/or ion-dipole interactions between at least one exogenous amine and the endogenous compounds present in the plant and/or animal and/or prokaryotic biological material.

Step (iii)

The eutectic extract obtained in step (ii) may optionally be separated from solids present in the mixture that have not complexed with the at least one exogenous amine. Any methods known in the art may be used, such as filtration.

For the avoidance of doubt, preferences, options, particular features and the like indicated for a given aspect, feature or parameter of the invention should, unless the context indicates otherwise, be regarded as having been disclosed in combination with any and all other preferences, option, particular features and the like as indicated for the same or other aspects, features and parameters of the invention.

Unless otherwise stated herein, the weight percentages listed are based on the total weight of the extract, for example the total weight of the at least one exogenous amine and/or the total weight of the plant and/or animal and/or prokaryotic biological material.

The term "about" as used herein, e.g. when referring to a measurable value (such as an amount of weight of a particular component in the composition or reaction mixture), refers to variations of ±20%, ±10%, ±5%, ±1%, ±0.5%, or particularly, ±0.1%, of the specified amount.

The eutectic extract obtained in step (ii) or (iii) may also be optionally purified using the purification process described below.

For example, the process for preparing a liquid, gel or gel-like eutectic extract may include a purification process after step (ii) and/or step (iii) comprising:

a) mixing the eutectic extract obtained in step (ii) or (iii) with a liquid that is immiscible with the eutectic extract;

b) allowing the mixture formed in step (a) to equilibrate into two phases; and c) separating the eutectic phase from the phase containing the liquid that is immiscible with the eutectic extract or eutectic combination.

The liquid that is immiscible in the eutectic extract or eutectic combination may be a lipid that is in a liquid form. For example, free fatty acids (e.g. oleic acid), free fatty alcohols, triacylglycerols, or vegetable oil (e.g. sunflower oil, canola oil).

Alternatively, the liquid that is immiscible in the eutectic extract or eutectic combination may be an alcohol, such as methanol or ethanol, an aliphatic organic solvent such as hexane, a terpenic solvent such as limonene or para-menthane, an aromatic organic solvent, such as benzene or toluene, or any solvent immiscible with the raw eutectic extract.

In the purification process of the invention, the ratio of eutectic extract to immiscible liquid is from about 1:0.1 to about 1:10, preferably from about 1:0.5 to about 1.2.

The purification process of the invention allows for the removal of exogenous amine that has not formed a complex through hydrogen bonding and/or ion-dipole interactions with the endogenous compounds in the biological material. The purification process may also be used to concentrate the active compounds present.

For example, the concentration of antioxidant compounds present in the eutectic extract may be increased resulting in the ORAC and CAT values of the eutectic extract increasing by about 10%, such as by about 20%, 30%, 40%, 50%, 60%, 70%, 80%, 90% or 100%.

Purification Process

The present inventors have also surprisingly and unexpectedly found that eutectic extracts, such as the eutectic extract obtained in-situ described above, can be purified to concentrate the active compounds present in the eutectic extract and increase the activity of the eutectic extract. For example, increase the antioxidant activity of the eutectic extract.

The present invention therefore provides a process for the purification of a eutectic extract or eutectic combination, hereinafter referred to as the purification process of the invention.

The present invention provides a purification process comprising:

a) mixing a eutectic extract or eutectic combination with a liquid that is immiscible with the eutectic extract or eutectic combination;

b) allowing the mixture formed in step (a) to equilibrate into two phases; and c) separating the eutectic phase from the phase containing the liquid that is immiscible with the eutectic extract or eutectic combination.

If required, the purification process may be repeated using the separated eutectic phase as the eutectic extract or eutectic combination in step (a).

Typically, the eutectic phase is the lower of the two equilibrated phases. However, this may depend on the liquid that is immiscible with the eutectic extract or eutectic combination.

The eutectic extract or eutectic combination may be prepared using the extraction process of the invention described previously or may be a eutectic extract or eutectic combination that has been prepared using other means, for example, a eutectic extract that has been prepared by extracting a biological material using a pre-prepared eutectic solvent.

The liquid that is immiscible in the eutectic extract or eutectic combination may be a lipid that is in a liquid form. For example, free fatty acids (e.g. oleic acid), free fatty alcohols, triacylglycerols, or vegetable oil (e.g. sunflower oil, canola oil).

Alternatively, the liquid that is immiscible in the eutectic extract or eutectic combination may be an alcohol, such as methanol or ethanol, an aliphatic organic solvent such as hexane, a terpenic solvent such as limonene or para-menthane, an aromatic organic solvent, such as benzene or toluene, or any solvent immiscible with the raw eutectic extract.

In the purification process of the invention, the ratio of eutectic extract to immiscible liquid is from about 1:0.1 to about 1:10, preferably from about 1:0.5 to about 1.2.

The purification process of the invention allows for the removal of exogenous amine that has not formed a complex through hydrogen bonding and/or ion-dipole interactions with the endogenous compounds in the biological material. The purification process may also be used to concentrate the active compounds present.

For example, the concentration of antioxidant compounds present in the eutectic extract may be increased resulting in the ORAC and CAT values of the eutectic extract increasing by about 10%, such as by about 20%, 30%, 40%, 50%, 60%, 70%, 80%, 90% or 100%.

Eutectic Extract

The present invention provides a liquid or a gel/gel-like eutectic extract obtained using the process for preparing a liquid, gel or gel-like eutectic extract of the invention as described previously, which may be referred to hereafter as the "extract of the invention".

The present invention also provides a liquid or gel/gel-like eutectic extract that has been purified using the purification process of the invention as described previously, which may be referred to hereinafter as the "purified extract of the invention".

The present invention is also directed to a liquid or a gel/gel-like eutectic combination of at least one exogenous amine and plant and/or animal and/or prokaryotic biological material, wherein the amine and biological material are present in a mass ratio of amine:biological material of from about 1:1 to about 10:1, such as from about 2:1 to about 8:1 or from about 4:1 to about 6:1, which may be referred to hereafter as the "combination of the invention".

The present invention is also directed to a liquid or a gel/gel-like eutectic combination of at least one exogenous amine and plant and/or animal and/or prokaryotic biological material that has been purified using the purification process of the invention, wherein the amine and biological material are present in a mass ratio of amine:biological material of from about 1:1 to about 5:1 or from about 1:1 to about 1:5, such as from about 1.5:1 to about 4:1 or from about 1:1.5 to 1:4, which may be referred to hereafter as the "purified combination of the invention".

In the eutectic extract or eutectic combination or purified eutectic extract or eutectic combination of the invention, the at least one exogenous amine is selected from the group consisting of quaternary ammoniums, pyridinium amines, alkylimidazolium amines and mixtures thereof. For example, the at least one exogenous amine may be selected from the group consisting of choline chloride, benzyltriethyl ammonium chloride, benzyltrimethyl ammonium chloride, carnitine, betaine and 1-butyl-3-methylimidazolium chloride and mixtures thereof.

In the eutectic extract or eutectic combination or purified eutectic extract or eutectic combination of the invention, the biological material is preferably plant biological material. The plant biological material may be obtained from or obtainable from plant roots, aerial parts, leaves, flowers, stems, barks, fruits or seeds or their tissues. For example, the fruit tissue may be the rind of the fruit. Aerial parts of the plant biological material may be preferred, such as the leaves of the plant.

In the eutectic extract or eutectic combination or purified eutectic extract or eutectic combination of the invention, the plant biological material may be obtained from or obtainable from Lamiaceae (including rosemary, *Salvia*, or any other species from the Lamiaceae family), *Citrus*, tree barks (such as *Cedrus* bark), *Choisya* (such as *Choisya×dewitteana* 'Aztec Pearl' (*Choisya ternate*)), Blueberry (*Cyanococcus*) (such as dried Blueberry), *Capsicum* (*Capsicum annuum*), Green chilli (*Capsicum frutescens*), Aubergine (*Solanum melongena*) (such as dried Aubergine), Ginger (*Zingiber officinale*), Cilantro, *Ziziphus, silybum marianum* (milk thistle) and *Orthosiphon*.

The eutectic extract or eutectic combination or purified eutectic extract or eutectic combination may contain natural compounds endowed with properties of cosmetic or nutritional interest such as natural flavourings, taste modifiers, fragrances, biocides, antimicrobials, proteins, enzymes, colourings, pigments, surfactants, chelatants, antioxidants, vitamins and mixtures thereof.

Typically, the natural compounds endowed with properties of cosmetic or nutritional interest such as natural flavourings, taste modifiers, fragrances, biocides, antimicrobials, proteins, enzymes, colourings, pigments, surfactants, chelatants, antioxidants, vitamins and mixtures thereof are present in the eutectic extract or eutectic combination or purified eutectic extract or eutectic combination as phenolic compounds (including phenolic acids, phenolic esters, phenolic diterpernes, flavonoids, secoiridoids, stilbenes and phenolic alcohols), as well as essential oils, terpenoids (including mono-, sesqui-, di-, tri-, and tetra-terpenoids such as carotenoids), alkaloids, lipids, phenylpropanoids, and mixtures thereof.

For example, active compounds present in eutectic extracts or eutectic combinations obtained using rosemary include, but are not limited to:

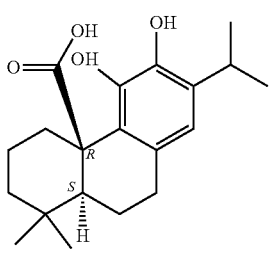
Carnosic acid
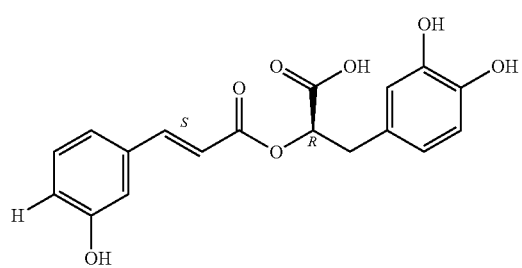
Rosmarinic acid
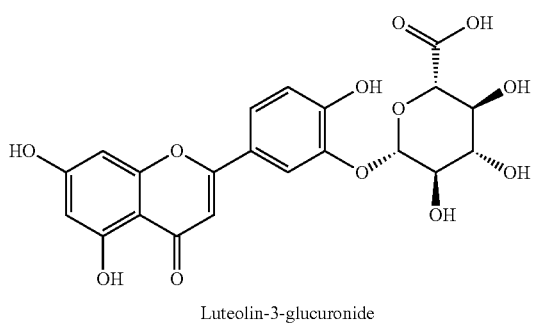
Luteolin-3-glucuronide
Active compounds present in eutectic extracts or eutectic combinations obtained using *Choisya* include, but are not limited to:
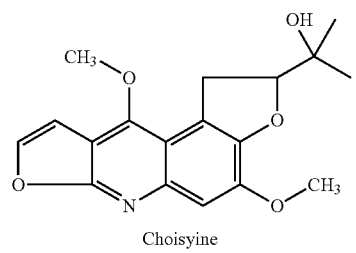
Choisyine
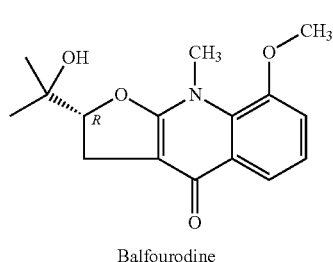
Balfourodine
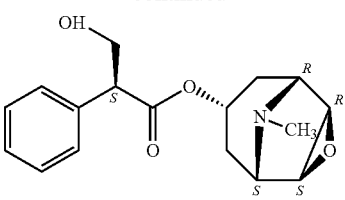
(-)-Scopolamine
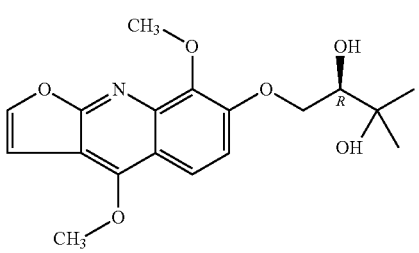
Evoxine
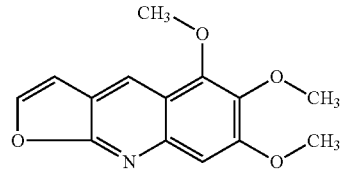
Kokusaginin
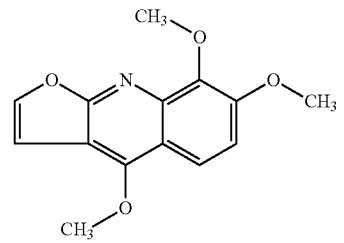
Skimmianin
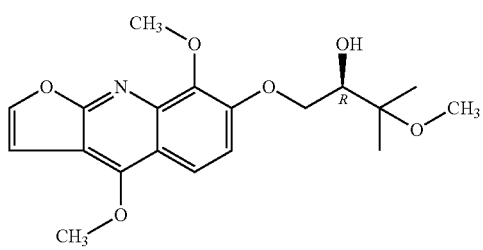
Methylevoxine
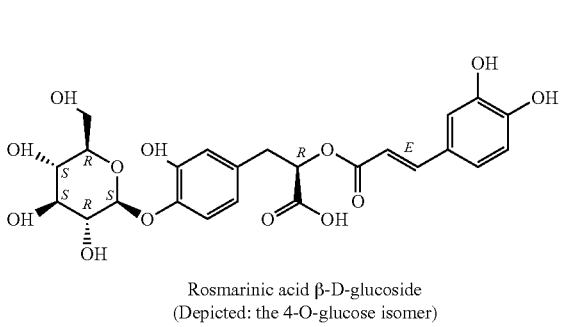
Rosmarinic acid β-D-glucoside
(Depicted: the 4-O-glucose isomer)

-continued
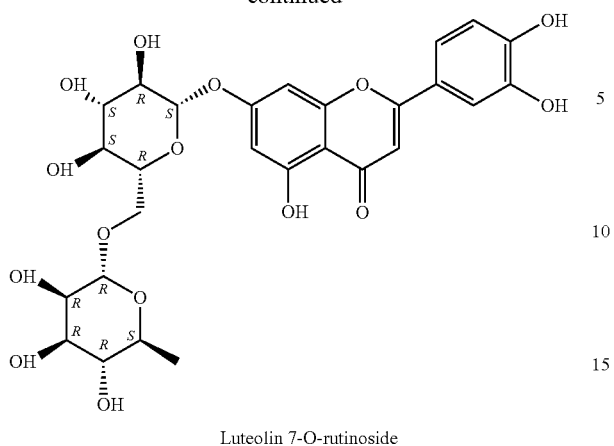
Luteolin 7-O-rutinoside
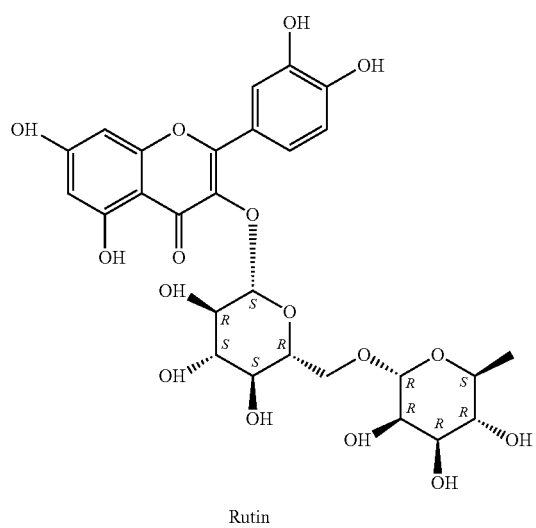
Rutin
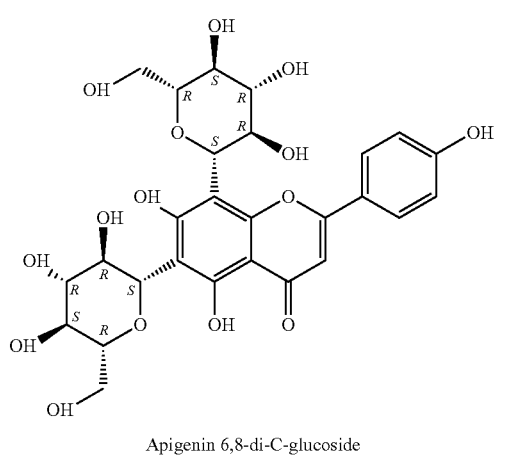
Apigenin 6,8-di-C-glucoside
Active compounds present in eutectic extracts or eutectic combinations obtained using lime include, but are not limited to:
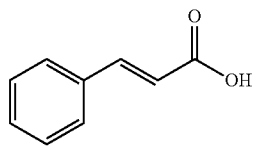
Cinnamic acid
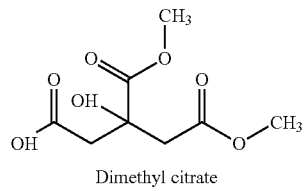
Dimethyl citrate
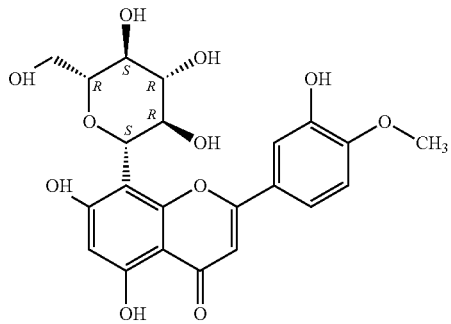
Diosmetin 8-C-glucoside
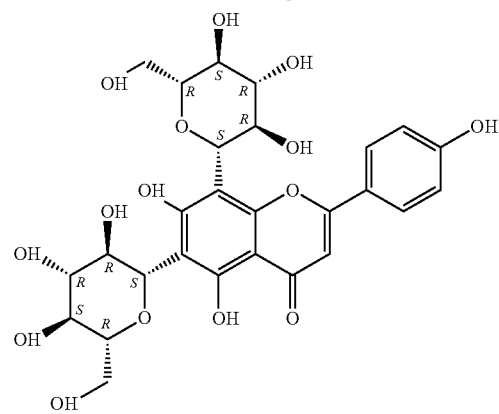
Apigenin 6,8-di-C-glucoside
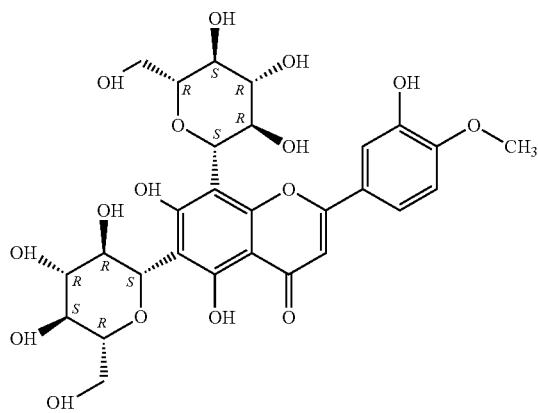
Diosmetin 6,8-di-C-glucoside

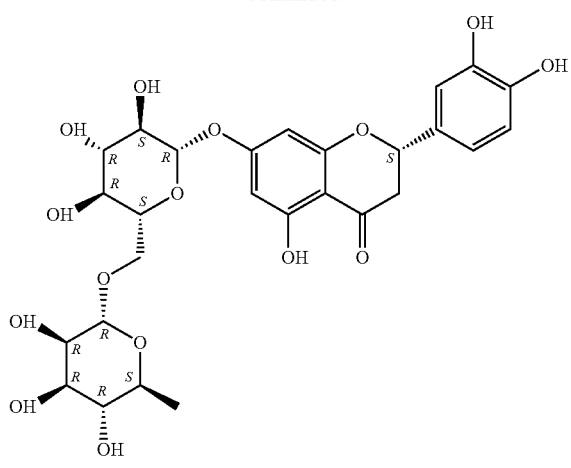
Eriodictyol 7-O-rutinoside
(Eriocitrin)
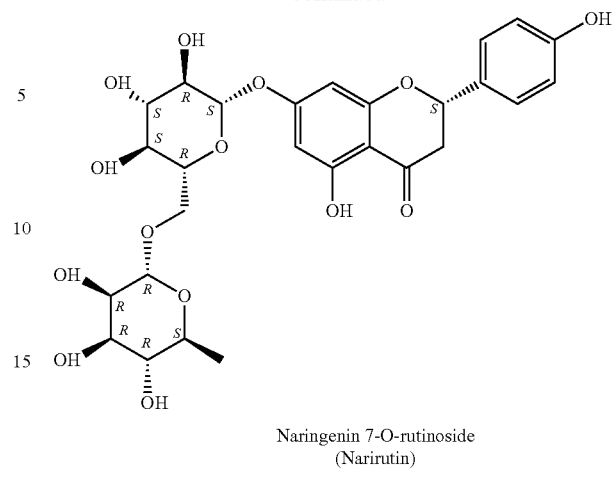
Naringenin 7-O-rutinoside
(Narirutin)
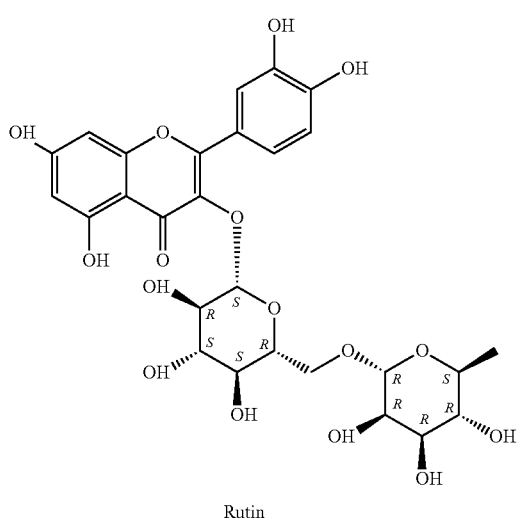
Rutin
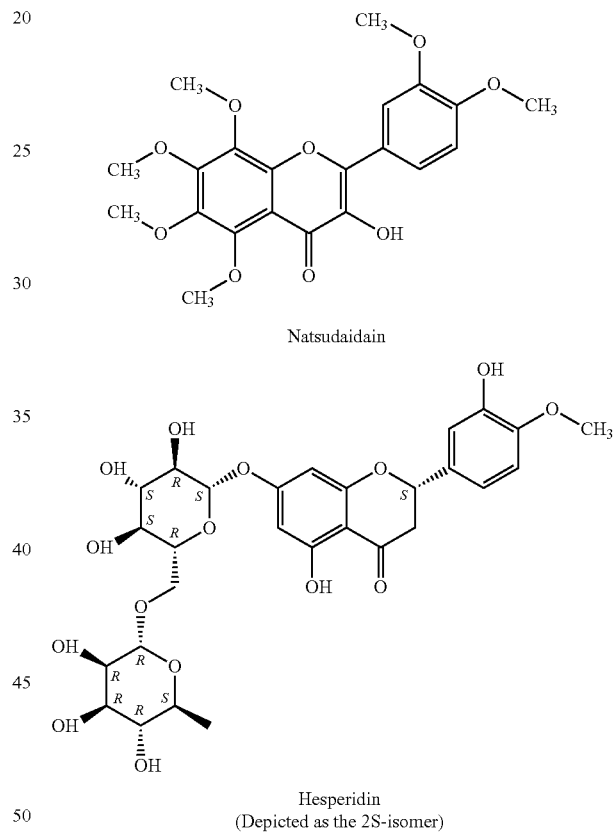
Natsudaidain
Hesperidin
(Depicted as the 2S-isomer)
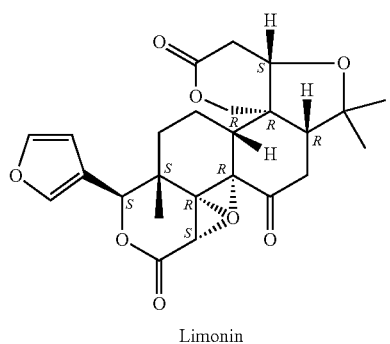
Limonin
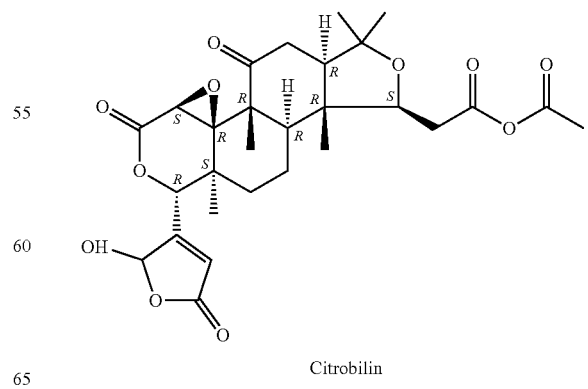
Citrobilin -continued

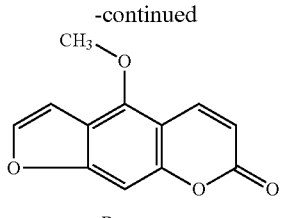

Bergapten

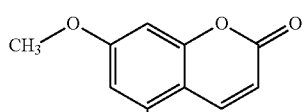

Citropten

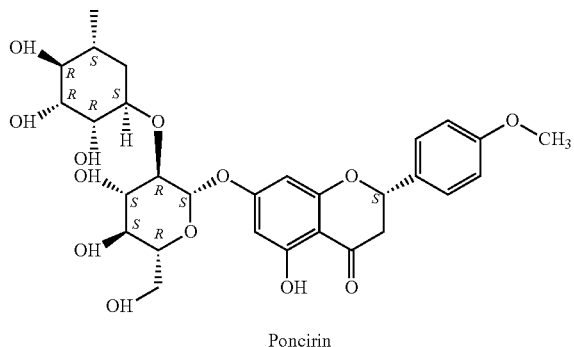

Poncirin

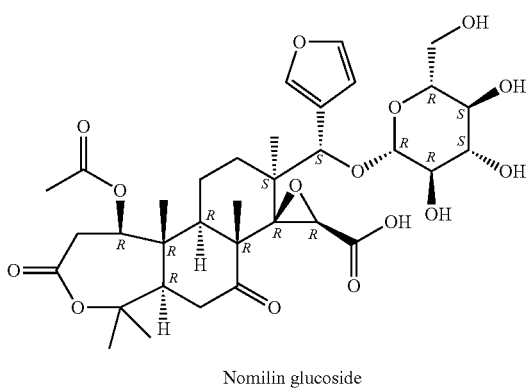

Nomilin glucoside

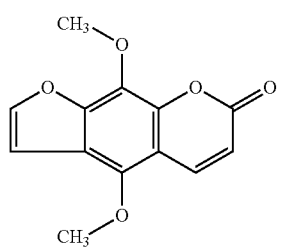

Isopimpinellin

-continued

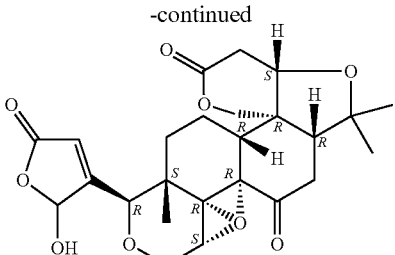

Limonexin

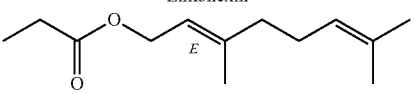

Geranyl propionate

In the extract or combination or purified extract or combination of the invention, the biological material comprises at least one endogenous compound capable of forming a complex with the at least one exogenous amine. The complex formed between the at least one endogenous compound in the biological material and the at least one exogenous amine may be formed via hydrogen bonds and/or ion-dipole interactions.

The at least one endogenous compound may be selected from the group consisting of amino acids, peptides, proteins, carbohydrates, fatty acids, triacylglycerols or other lipids, vitamins, organic acids, polyols, enols, alkaloids, secoiridoids, terpenoids, phenolic compounds and mixtures thereof.

Uses of the Eutectic Extract or Eutectic Combination or Purified Eutectic Extract or Eutectic Combination of the Invention The eutectic extract or eutectic combination or purified eutectic extract or eutectic combination of the invention may be used to provide natural compounds endowed with properties of cosmetic or nutritional interest such as natural biological flavourings and taste modifiers, fragrances, biocides, antimicrobials, proteins, enzymes, colourings, pigments, surfactants, chelatants, antioxidants, vitamins and mixtures thereof from plant and/or animal and/or prokaryotic biological material, and preferably from plant biological material.

Typically, the natural compound endowed with properties of cosmetic or nutritional interest such as natural biological flavourings and taste modifiers, fragrances, biocides, antimicrobials, proteins, enzymes, colourings, pigments, surfactants, chelatants, antioxidants, vitamins and mixtures thereof are present in the eutectic extract or eutectic combination or purified eutectic extract or eutectic combination as phenolic compounds (including phenolic acids, phenolic esters, phenolic diterpernes, flavonoids, secoiridoids, stilbenes and phenolic alcohols), as well as essential oils, terpenoids (including mono-, sesqui-, di-, tri-, and tetra-terpenoids such as carotenoids), alkaloids, lipids, phenylpropanoids, and mixtures thereof, from plant and/or animal and/or prokaryotic biological material, and preferably from plant biological material.

For example, the eutectic extract or eutectic combination or purified eutectic extract or eutectic combination of the invention may be high in compounds that provide antioxidant activity.

Thus, the present invention provides a eutectic extract or eutectic combination or purified eutectic extract or eutectic combination comprising antioxidants obtained from plant and/or animal and/or prokaryotic biological material.

The present invention also provides the use of a eutectic extract or eutectic combination or purified eutectic extract or eutectic combination as an anti-oxidant. The antioxidant may be used in the compositions and/or products as described below.

The eutectic extract or eutectic combination or purified eutectic extract or eutectic combination of the invention may be used to provide a nutraceutical composition, a dietary or food product for humans or animals (such as functional food compositions, i.e. food, drink, feed or pet food or a food, drink, feed or pet food supplements), a nutritional supplement, a fragrance or flavouring, a pharmaceutical (pharmaceutical compositions or formulations), a veterinary composition, an oenological or a cosmetic formulation.

The nutraceutical composition, dietary or food product for humans or animals (such as functional food compositions, i.e. food, drink, feed or pet food or a food, drink, feed or pet food supplements), nutritional supplement, fragrance or flavouring, pharmaceutical (pharmaceutical compositions or formulations), veterinary composition, oenological or cosmetic formulation may be administered orally or parenterally, or for topical, rectal, nasal, auricular, vaginal and/or ocular application.

The present invention therefore provides a eutectic extract or eutectic combination or purified eutectic extract or eutectic combination for use in nutraceutical compositions, dietary or food products for humans or animals (such as functional food compositions, i.e. food, drink, feed or pet food or a food, drink, feed or pet food supplements), nutritional supplements, fragrances or flavourings, pharmaceuticals (pharmaceutical compositions or formulations), veterinary compositions, oenological or cosmetic formulations.

The present invention also provides nutraceutical compositions, dietary or food products for humans or animals (such as functional food compositions, i.e. food, drink, feed or pet food or a food, drink, feed or pet food supplements), nutritional supplements, fragrances or flavourings, pharmaceuticals (pharmaceutical compositions or formulations), veterinary compositions, oenological or cosmetic formulations comprising the eutectic extract or eutectic combination or purified eutectic extract or eutectic combination of the invention, and optionally a pharmaceutically/veterinary acceptable ingredients, such as excipients or carriers or (functional) food acceptable ingredients and mixtures thereof, as appropriate.

As used herein, references to pharmaceutically or veterinary acceptable excipients may refer to pharmaceutically or veterinary acceptable adjuvants, diluents and/or carriers as known to those skilled in the art.

Food acceptable ingredients include those known in the art (including those also referred to herein as pharmaceutically acceptable excipients) and can be natural or non-natural, i.e. their structure may occur in nature or not. In certain instances, they can originate from natural compounds and be modified before use (e.g. maltodextrin).

By "pharmaceutically or veterinary acceptable" we mean that the additional components of the composition are generally safe, non-toxic, and neither biologically nor otherwise undesirable. For example, the additional components are generally sterile and pyrogen free. Such components must be "acceptable" in the sense of being compatible with the extract of the invention and not deleterious to the recipients thereof. Thus, "pharmaceutically acceptable excipients" includes any compound(s) used in forming a part of the formulation that is intended to act merely as an excipient, i.e. not intended to have biological activity itself.

The skilled person will understand that extracts of the invention (e.g. in the form of compositions, such as pharmaceutical or veterinary compositions) may be administered to a patient or subject (e.g. a human or animal patient or subject) by any suitable route, such as by the oral, rectal, nasal, pulmonary, buccal, sublingual, transdermal, intracisternal, intraperitoneal, or parenteral (including subcutaneous, intramuscular, intrathecal, intravenous and intradermal) route.

Extracts of the invention may be administered orally. In such instances, pharmaceutical or veterinary compositions according to the present invention may be specifically formulated for administration by the oral route.

Pharmaceutical or veterinary compositions for oral administration include solid dosage forms such as hard or soft capsules, tablets, troches, dragees, pills, lozenges, powders and granules. Where appropriate, they can be prepared with coatings such as enteric coatings, or they can be formulated so as to provide controlled release of the active ingredient, such as sustained or prolonged release, according to methods well known in the art.

Liquid dosage forms for oral administration include solutions, emulsions, aqueous or oily suspensions, syrups and elixirs.

Compositions (e.g. pharmaceutical or veterinary or food compositions) described herein, such as those intended for oral administration, may be prepared according to methods known to those skilled in the art, such as by mixing the components of the composition together.

The compositions of the invention may contain one or more additional ingredients, such as food ingredients or pharmaceutical ingredients and excipients, such as sweetening agents, flavouring agents, colouring agents and preserving agents. The compositions of the invention may contain the active ingredient(s) in admixture with non-toxic pharmaceutically acceptable excipients (or ingredients) which are suitable for the manufacture of tablets. These excipients (or ingredients) may, for example, be: inert diluents, such as calcium carbonate, sodium carbonate, lactose, calcium phosphate or sodium phosphate; granulating and disintegrating agents, for example, corn starch, maltodextrin or alginic acid; binding agents, for example, starch, gelatine or acacia; or lubricating agents, for example magnesium stearate, stearic acid, talc and mixtures thereof.

Solid compositions of the invention may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

Liquid compositions of the invention may be contained within a capsule, which may be uncoated or coated as defined above.

Suitable pharmaceutical or veterinary carriers include inert solid diluents or fillers, sterile aqueous solutions and various organic solvents. Examples of solid carriers are lactose, terra alba, sucrose, cyclodextrin, maltodextrin, talc, gelatin, agar, pectin, acacia, magnesium stearate, stearic acid, arabic gum, modified starch and lower alkyl ethers of cellulose, saccharose, silica and mixtures thereof. Examples of liquid carriers are syrup, peanut oil, olive oil, phospholipids, fatty acids, fatty acid amines, polyoxyethylene and water.

Moreover, the carrier or diluent may include any sustained release material known in the art, such as glyceryl monostearate or glyceryl distearate, alone or mixed with a wax.

Suitable pharmaceutical carriers include inert solid diluents or fillers, sterile aqueous solutions and various organic solvents. Examples of solid carriers are lactose, terra alba, sucrose, cyclodextrin, maltodextrin, dextrin, talc, gelatine, agar, pectin, acacia, magnesium stearate, magnesium hydroxide; stearic acid, arabic gum, modified starch and lower alkyl ethers of cellulose, saccharose, silicon dioxide. Examples of liquid carriers are syrup, vegetables oils, phospholipids, fatty acids, fatty acid amines, polyoxyethylene and water. Moreover, the carrier or diluent may include any sustained release material known in the art, such as glyceryl monostearate or glyceryl distearate, alone or mixed with a wax.

The term "carrier" as used herein, may also refer to a natural product or a product originating from nature that has been transformed or modified so that it is distinct from the natural product from which it originated, such as maltodextrin.

Depending on the disorder, and the subject, to be treated, as well as the route of administration, extracts of the invention may be administered at varying doses (i.e. therapeutically effective doses, as administered to a patient in need thereof). In this regard, the skilled person will appreciate that the dose administered to a mammal, particularly a human, in the context of the present invention should be sufficient to affect a therapeutic response in the mammal over a reasonable timeframe. One skilled in the art will recognize that the selection of the exact dose and composition and the most appropriate delivery regimen will also be influenced by inter alia the pharmacological properties of the formulation, the nature and severity of the condition being treated, and the physical condition and mental acuity of the recipient, as well as the age, condition, body weight, sex and response of the patient to be treated, and the stage/severity of the disease.

The pharmaceutical or veterinary or food compositions comprise an extract of the invention in a therapeutically effective amount. As used herein, the term "effective amount" is synonymous with "therapeutically effective amount", "effective dose", or "therapeutically effective dose" and when used in the present invention refers to the minimum dose of the extract of the invention necessary to achieve the desired therapeutic effect and includes a dose sufficient to reduce a symptom associated with inflammation. Effectiveness in treating the diseases or conditions described herein can be determined by observing an improvement in an individual based upon one or more clinical symptoms, and/or physiological indicators associated with the condition. An improvement in the diseases or conditions described herein also can be indicated by a reduced need for a concurrent therapy.

Additionally, where repeated administration of the extract of the invention is used, an effective amount of the extract of the invention will further depend upon factors, including, without limitation, the frequency of administration, the half-life of the extract of the invention, or any combination thereof.

The amount of the eutectic extract or eutectic combination present in nutraceutical compositions, dietary or food products for humans or animals (such as functional food compositions, i.e. food, drink, feed or pet food or a food, drink, feed or pet food supplements), nutritional supplements, fragrances or flavourings, pharmaceuticals (pharmaceutical compositions or formulations), veterinary compositions, oenological or cosmetic formulations will vary depending on the application.

Typically, the amount of eutectic extract or eutectic combination present in nutraceutical compositions, dietary or food products for humans or animals (such as functional food compositions, i.e. food, drink, feed or pet food or a food, drink, feed or pet food supplements), nutritional supplements, fragrances or flavourings, pharmaceuticals (pharmaceutical compositions or formulations), veterinary compositions, oenological or cosmetic formulations will be from about 0.001 to about 50% by weight of the nutraceutical compositions, dietary or food product, nutritional supplement, fragrance or flavouring, pharmaceutical composition or formulation, veterinary composition, oenological or cosmetic formulation, such as from about 0.01 to about 10%, or from about 0.1 to 1%.

Pharmaceutical or veterinary or food compositions of the invention may consist of or consist essentially of the extract of the invention and pharmaceutical or veterinary or food composition.

For the avoidance of doubt, in this specification when we use the term "comprising" or "comprises" we mean that the extract or composition being described must contain the listed ingredient(s) but may optionally contain additional ingredients. When we use the term "consisting essentially of" or "consists essentially of" we mean that the extract or composition being described must contain the listed ingredient(s) and may also contain small (for example up to 5% by weight, or up to 1% or 0.1% by weight) of other ingredients provided that any additional ingredients do not affect the essential properties of the extract or composition. When we use the term "consisting of" or "consists of" we mean that the extract or composition being described must contain the listed ingredient(s) only.

EXAMPLES

The present invention will be further described by reference to the following, non-limiting examples.

Example 1—General Procedure for the Preparation of Eutectic Extract

Different parts of naturally occurring plants as well as fruits and plant barks were used to form deep eutectics with different amines.

The leaves used were sourced from rosemary (*Rosmarinus officinalis*) and *Choisya×dewitteana* 'Aztec Pearl' (*Choisya ternate*); fruits used were Lime (*Citrus aurantifolia*), Blueberry (*Cyanococcus*), Capsicum (*Capsicum annuum*), Green chilli (*Capsicum frutescens*) and Aubergine (*Solanum melongena*). Ginger (*Zingiber officinale*) was used as an example of plant root and barks of the *Cedrus* spp. tree was used as an example of bark.

The desired amount of each was ground using a mortar and pestle in the presence of liquid nitrogen to make the material brittle and easier to shatter.

Juicy fruits such as lime and blueberry were separated into juice and pulp by mechanical expulsion using a kitchen juicer and treated separately while *Capsicum* and green chilli were physically separated to seeds and skins before treatment. The aubergine skin was removed prior to treatment. The filtered juices were freeze dried (48 h) to give respective powders and some portion of the juices were also heat dried (50° C. for 48 h) to remove excess water.

The ground powders thus obtained were sieved (Fisherbrand Test Sieve, 1 mm) to form homogeneous fine powders.

Different amines were used to demonstrate the differences and specificities between aliphatic and aromatic amines:
  (i) Three quaternary ammonium salts: choline chloride (ChCl) (Sigma-Aldrich, >99%), and benzyltriethyl ammonium chloride (BTEAC), benzyltrimethyl ammonium chloride (BTMAC) (Sigma-Aldrich, 99%),
  (ii) one quaternary ammonium zwitterion: betaine (Sigma-Aldrich, 98%),
  (iii) and one dialkylimidazolium salt: 1-butyl-3-methylimidazolium chloride (Sigma-Aldrich, ≥98%) (BmimCl).

Figure 1:
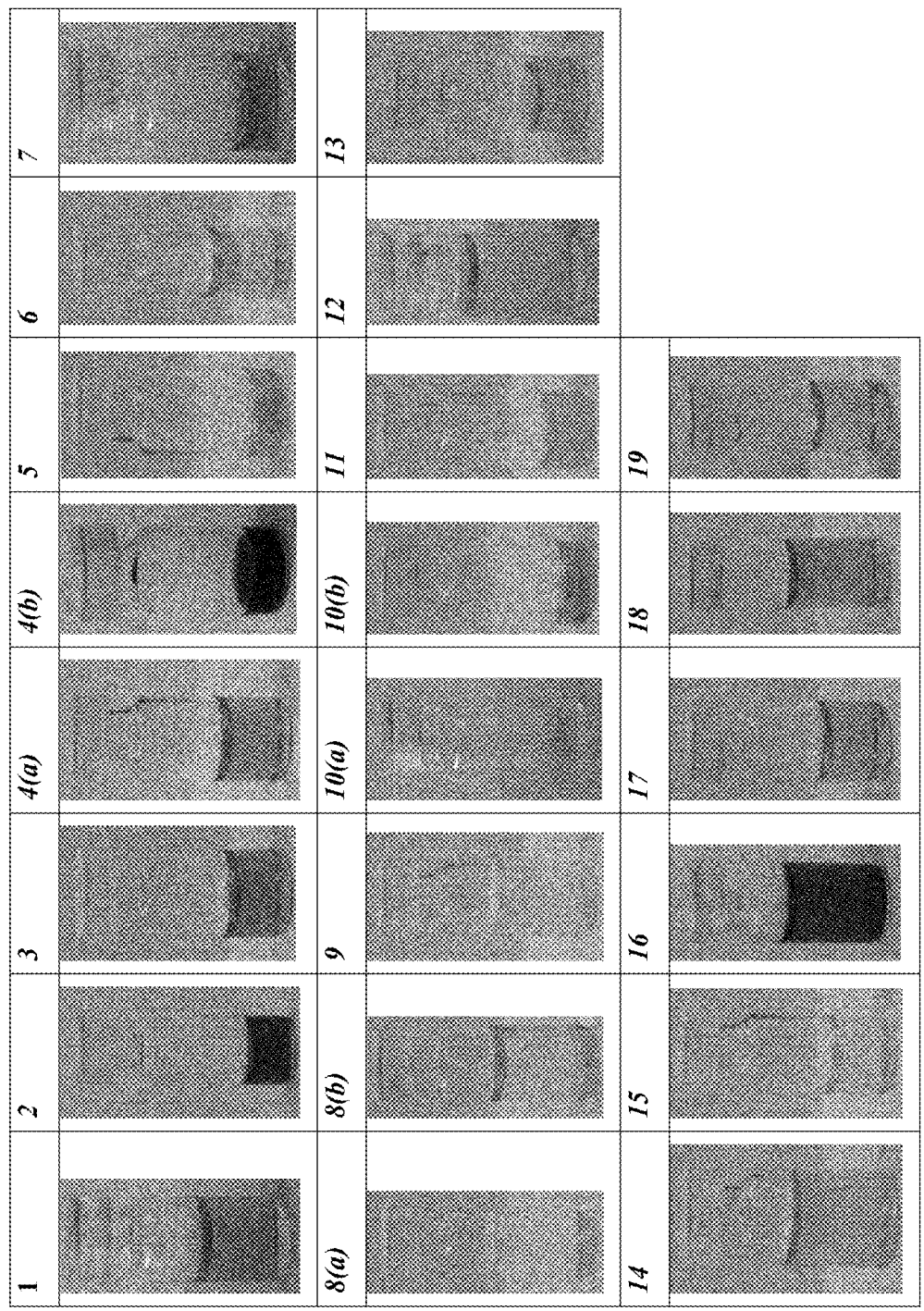
FIG. 1: Visual representations of the eutectic solvents obtained using the process of the invention.

The amines listed above in a solid state were mixed with the natural product powders in different mass ratios to produce in situ (i.e. during the extraction) eutectic mixtures by specifically interacting with the hydrogen bond donors (HBDs) present in the natural products. FIG. 1 illustrates some representative examples of the eutectic extracts formed in each of Examples 3A1 to 3A19 discussed below.

Example 2—General Procedure for the Analysis of Eutectic Extracts and Combination Measurement of the Antioxidant Activity and Identification and Quantification of Compounds of Interest by High Performance Liquid Chromatography (HPLC))

Test of Physico-Chemical Efficacy as Antioxidant—Oxygen Radical Absorbance Capacity (ORAC) Method The capacity of the raw or purified eutectic extracts to trap peroxyradicals was determined using the reference method published by Ou et al. (Determination of total antioxidant capacity by oxygen radical absorbance capacity (ORAC) using fluorescein as the fluorescent probe: First action 2012.23. Journal of AOAC International, 2013, 96, 1372-1376) in the AOAC Official Journal. For information, the AOAC is the Association of Official Agricultural Chemists of the United States Department of Agriculture (USDA).

Phosphate buffer solutions (pH 7.2) containing the desired concentrations of eutectic extracts were prepared. Fifty millilitres of each solution were transferred by multi-channel pipette into a Fluotrac 96-well microplate (Greiner). Each well was then topped up with 100 µL of phosphate buffer solution, pH 7.2, containing 0.126 µM of fluorescein disodiium salt.

To improve the repeatability, the microplate was preheated at 37° C. under orbital stirring at 1,200 rpm in a temperature-controlled thermoshaker (PHMT series, Grant Instruments Ltd, Shepreth, England) for 20 minutes.

50 µL of AAPH solution in freshly prepared phosphate buffer solution was then added using a multi-channel pipette.

Each well contained 200 µL of the final mixture which was composed of 0.063 M of fluorescein disodiium salt, 12.7 mM of AAPH and increasing concentrations of eutectic extracts in phosphate buffer solution.

A drop in fluorescence to 515 nm ($\lambda$ex: 490 nm) was immediately recorded. Measurements were then taken every minute for 2 hours at 37±0.1° C. with 5 seconds of stirring before each measurement using a microplate reader. The results were then calculated according to Ou et al. Development and validation of an improved oxygen radical absorbance capacity using fluorescein as the fluorescent probe. J. Agric. Food Chem. 2001, 49, 4619-4626) in µmol of Trolox equivalent per g of liquid extract (ORAC value).

General Method for the Conjugated Autoxidizable Triene (CAT) Assay Used in the Following Examples Antioxidant capacity of raw or purified eutectic extracts was measured using the CAT procedure described by (Laguerre M, López-Giraldo L J, Lecomte J, Baréa B, Cambon E, Tchobo P F, Barouh N, Villeneuve P. Conjugated autoxidizable triene (CAT) assay: a novel spectrophotometric method for determination of antioxidant capacity using triacylglycerol as ultraviolet probe. Anal Biochem. 2008, 380, 282-290) with slight modifications.

Antioxidant solutions were prepared as follows: a methanol solution of eutectic extract or Trolox (reference) was prepared at the desired concentration. The eutectic extract solutions were filtered (0.45 µm) to remove impurities which can interfere in the CAT value measurement.

Various volumes of this solution (25, 50, 75, and 100 µL) were then added to 24.9 mL of phosphate buffer solution (PBS), pH 7.2, and then filled to 25.0 mL with pure methanol (75, 50, 25, and 0 µL, respectively).

In this way, all buffered solutions of eutectic extract contained the same methanol volume (100 µL), which minimizes any possible bias among samples.

Samples of these solutions (50 µL/well) were transferred using a multichannel micropipet into UV-Star 96-well microplate (Greiner, Frickenhausen, Germany) (absorbance at 273 nm=0.03). The microplate was then prewarmed and stirred in a thermostated shaker (PHMT Grant Instruments, Shepreth, England) at 37° C. for 5 min at 1,200 rpm.

Twenty-five milliliters of a buffered solution (pH 7.2) containing 34 µM Brij 35 (neutral emulsifier, estimated MW=1,198 g/mol) was added to 5 mg tung oil (non-stripped) in a brown glass flask.

For the next step, this mixture was stirred for 10 s using a Vortex apparatus, before its homogenization in an Ultra Turrax homogenizer (Janke & Kunkel, Staufen, Germany) at approximately 2,400 rpm for 90 s.

Each well was then filled with 100 µL of this tung oil-in-PBS emulsion. To improve repeatability, the microplate was then immediately pre-warmed and shaken, sheltered from light, in a thermostated shaker (PHMT Grant Instruments) at 37° C. for 1 min at 1,200 rpm.

Fifty microliters of a freshly prepared AAPH solution in PBS (4 mM) was added with a multi-channel micropipet.

In the end, each well contained 200 µL of the final mixture consisting of 115 µM stripped tung oil, 17 µm Brij 35, 1 mM AAPH, and various concentrations of Trolox (from 0 to 2 µM) and eutectic extracts in PBS. The progress of reactions was immediately monitored by recording the decrease in absorbance at 273 nm. Measurements were performed each minute for 5 h at 37±0.1° C., with 5 seconds of stirring before each measurement, using a Saffire 2 microplate reader (Tecan, Groedig, Austria) equipped with Magellan software.

Each experiment was performed in triplicate (three wells), and results were expressed as the mean of CAT value (see below) ±SD.

Similarly, to the ORAC assay, the antioxidant value of a sample was calculated through the difference between the area under the curve of this sample and that of the blank (without eutectic extract). The result of this operation gave the net area under the curve (AUC) which was then plotted on a graph as a function of the concentration. Only the linear part of the curve was taken into account to calculate the slope which was then divided by the slope of the Trolox (standard) calculated in the same conditions and analyzed on the same microplate. As such, CAT values were expressed as µmol Trolox equivalent/g eutectic extract.

Example of HPLC-ESI/MS Analysis—Identification of the Main Compounds Contained in the Chemical Profile of the Liquid Extracts of Choisya and Lime The chromatographic conditions hereinbelow were applied with a view to identifying and quantifying the compounds present in the various extracts produced.

Column: Waters BEH C18 50 mm×2.1 mm 1.7 µm
Temperature: 45° C.
Flow: 0.3 mL/min
Injection volume: 2 µL
Negative mode
Mobile phase: A: 0.1% formic acid in acetonitrile
B: 0.1% formic acid in Water

| Time (min) | A % | B % |
|---|---|---|
| 0 | 10 | 90 |
| 20 | 10 | 90 |
| 30 | 90 | 10 |

Note: Re-Equilibrate at Starting Mobile Phase Conditions for at Least 10 Minutes Between Each Run Sample preparation: 100 mg of DES were diluted into 5 ml of methanol/water (50:50), filtered and injected into LC system Example of HPLC-DAD Analysis—the Concentration of Rosmarinic Acid in the Liquid Extracts of Rosemary The liquid extracts obtained using the method described in Example 1 were analyzed directly by HPLC without preliminary concentration or drying.

Quantification and identification of rosmarinic acid are performed using an analytical standard (Extrasynthese—reference: 4957S) and by plotting a calibration curve. The Agilent 1100 HPLC apparatus is equipped with a UV-Visible DAD detector or equivalent. An elution gradient is used via a mixture of HPLC grade acetonitrile and HPLC grade water with an addition of 99% trifluoroacetic acid (TFA). The following chromatography conditions are used:

Zorbax Eclipse XDB C18 column, 1.8µm$_f$, 4.6 mm×50 mm or equivalent.

Mobile phase:

| Time (min) | % acetonitrile 0.1% TFA | % water 0.1% TFA |
|---|---|---|
| 0 | 15 | 85 |
| 2 | 15 | 85 |
| 2.5 | 18 | 82 |
| 2.7 | 100 | 0 |
| 3.5 | 100 | 0 |

Flowrate: 2 mL/min.
Detection: 328 nm
Temperature: 60° C.
Injection volume: 2 pL
Pressure: 210 bars±5 bars The following retention times are observed:
Rosmarinic acid: 2.0 min; Luteolin 3-glucuronide: 2.3 min.

Example of Gas Chromatography (GC) Analysis Coupled to a Flame Ionization Detector (FID)—the Concentration of Oleic Acid in the Upper and Lower Phases after the Purification Process Applied to a Raw Eutectic Extract The liquid phases (upper and lower) obtained using the purification method described in Examples 3B1 to 3B3 were prepared for the analysis as follows: 50 mg of each liquid phase were dispensed into a 20 mL glass autosampler vial, then added with 1 mL of the internal standard (methyl pentadecanoate) and 4 mL of 0.5 N NaOH solution in methanol. Before being hermetically closed with a septum, vials were flushed with nitrogen then stirred and heated at 100° C. for 5 min. The samples were then allowed to cool down to room temperature then opened carefully and 5 mL of a 14% BF3 solution in methanol was added. The samples were then flushed with nitrogen before being closed, stirred and heated at 100° C. for 30 min with stirring starting at 15 min. The samples were then allowed to cool down to room temperature then opened and 4 mL of a 10% NaCl aqueous solution and 4 mL of pure n-hexane was added. The samples were then vortexed and centrifuged at 3000 rpm for 3 min. The resulting upper phase was transferred into 2 mL-vials, then placed on a autosampler for GC-FID analysis.

The samples were analyzed using a 7890 Agilent gas chromatograph equipped with autosampler and a RTX®-capillary column (2330 60 m×0.25 mm with 0.20 µm film thickness). Injector temperature was set at 250° C. in a split mode (1:50) and with a liner (ref 092003, SGE Analytical Sciences). The GC oven temperature was set at 120° C. for 5 min, ramped to 200° C. at a rate of 5° C./min, held at 200° C. for 10 min, then ramped to 230° C. at a rate of 2° C./min and finally held at 230° C. for 15 min. Helium at 2 mL/min was used as the carrier gas (constant pressure at 30 psi). FID temperature was set at 300° C.

Example 3—Specific Examples of Eutectic Extracts

Examples of methods used to produce eutectic extracts, and more preferably to produce highly active and concentrated liquid eutectic extracts, are set out below as Examples 3A and 3B.

Examples 3A are a set of 19 generic examples demonstrating the feasibility of the eutectigenesis-assisted extraction process on a diverse range of biological raw materials such as seeds, peels, juice, whole fruits, veggies, roots, leaves, and barks.

Examples 3B are a set of results exemplifying the enhancement of the extract activity and profile using the purification process.

Examples 3A

Example 3A1: Fresh Rosemary Leaves (*Rosmarinus officinalis*)+Amines

Fresh rosemary leaves were ground using liquid $N_2$ then mixed with choline chloride and left at 20° C. in an open crystallising dish for five days. At the end of this period, a liquid had formed in the dish. Optimal weight ratios of amine to fresh rosemary were found to 1 to 10 times.

Example 3A1 is the result of combining 0.5 g of fresh rosemary powder and 2.0 g of choline chloride (ChCl) (weight ratio: 1:4, resp.).

Other eutectic extracts were obtained from fresh rosemary. Some with a different weight ratio with ChCl (1:2, 1:6, and 1:8) and another with benzyltriethylammonium chloride (BTEAC) (1:2).

In all cases, the liquid was separated from the biomass components via centrifugation and analysed using the oxygen radical absorbance capacity (ORAC) and the conjugated autoxidizable triene (CAT) methods. Results show that they exert antioxidant activity, which suggests that phytoactive compounds were extracted from fresh rosemary.

The antioxidant activities of the five extracts are shown in Table 1. As it can be seen, the more the amine (ChCl), the lower the antioxidant activity, which is probably due to a dilution effect of the antioxidant compounds by the amine.

TABLE 1

Compositions and antioxidant activities of different eutectic extracts.

| Natural Product Material | Added amine | Nat. product:amine weight ratio | Eutectic formation | ORAC value (μmol TE/g) | CAT value (μmol TE/g) |
|---|---|---|---|---|---|
| Fresh Rosemary | ChCl | 1:2 | Melt | 10.8 | 3.90 |
| Fresh Rosemary | ChCl | 1:2 (repetition) | Melt | 12.7 | — |
| Fresh Rosemary | ChCl | 1:4 | Melt | 7.4 | 2.2 |
| Fresh Rosemary | ChCl | 1:6 | Melt | 6.0 | 1.5 |
| Fresh Rosemary | ChCl | 1:8 | Melt | 4.6 | 1.60 |
| Fresh Rosemary | ChCl | 1:8 (repetition) | Melt | 5.7 | — |
| Fresh Rosemary | BTEAC | 1:2 | Melt | 24.3 | 7.70 |
| Fresh Rosemary | BTEAC | 1:2 (repetition) | Melt | 27.5 | — |
| — | ChCl alone | — | Powder | 0.3 | 0 |
| — | BTEAC alone | — | Powder | 2.8 | 0.7 |

Example 3A2: Dried Rosemary Leaves (*Rosmarinus officinalis* L.)+Amines

Dry rosemary leave powder was produced by freezing the rosemary leaves with liquid $N_2$ and grinding with a pestle and mortar. The resulting powder was mixed with different amines in different ratios to make deep eutectic mixtures and extract components which have ability to form hydrogen bonds with the tested amines.

The dried biomass was mixed with amines and left at room temperature in an open vessel for 10 days to extract as much natural product as possible.

Optimal weight ratios of amines to dried rosemary were found to 1 to 10 times. Example 3A2 is the result of combining 0.5 g of dried rosemary powder and 2.0 g of ChCl (weight ratio: 1:4, resp.).

At the end of this period (10 days) a large volume of coloured liquid had formed due to the hygroscopic nature of the amines. The liquid was analysed using HPLC and found to contain a variety of natural products extracted from the plant. The colour of the extract is noticeably darker than for the fresh rosemary which is due to the higher relative concentration of natural products in the dried biomass.

Other eutectic extracts were obtained from dried rosemary: some with a different weight ratio with ChCl (1:6), others with BTEAC (1:8) or 1-Butyl-3-methylimidazolium chloride (BmimCl) (1:4).

TABLE 2

Compositions and antioxidant activities of different eutectic extracts.

| Natural Product Material | Added amine | Nat. product:amine weight ratio | Eutectic formation | ORAC value (μmol TE/g) | CAT value (μmol TE/g) |
|---|---|---|---|---|---|
| Dried rosemary powder | ChCl | 1:4 | Melt | 84.3 | 22.9 |
| Dried rosemary powder | ChCl | 1:6 | Melt | 84.8 | 25.4 |
| Dried rosemary powder | ChCl | 1:8 | Melt | 106.9 | 21.0 |
| Dried rosemary powder | BTEAC | 1:8 | Melt | 81.2 | 23.9 |
| Dried rosemary powder | BTEAC | 1:8 (repetition) | Melt | 70.2 | 19.4 |
| Dried rosemary powder | BmimCl | 1:4 | Melt | 207.4 | 53.4 |
| Dried rosemary powder | BmimCl | 1:6 | Melt | 158.2 | 39.6 |
| Dried rosemary powder | BmimCl | 1:8 | Melt | 153.5 | 34.7 |
| — | ChCl alone | — | Powder | 0.3 | 0 |
| — | BTEAC alone | — | Powder | 2.8 | 0.7 |
| — | BmimCl alone | — | Powder | 1.1 | 0.24 |

Figure 2:
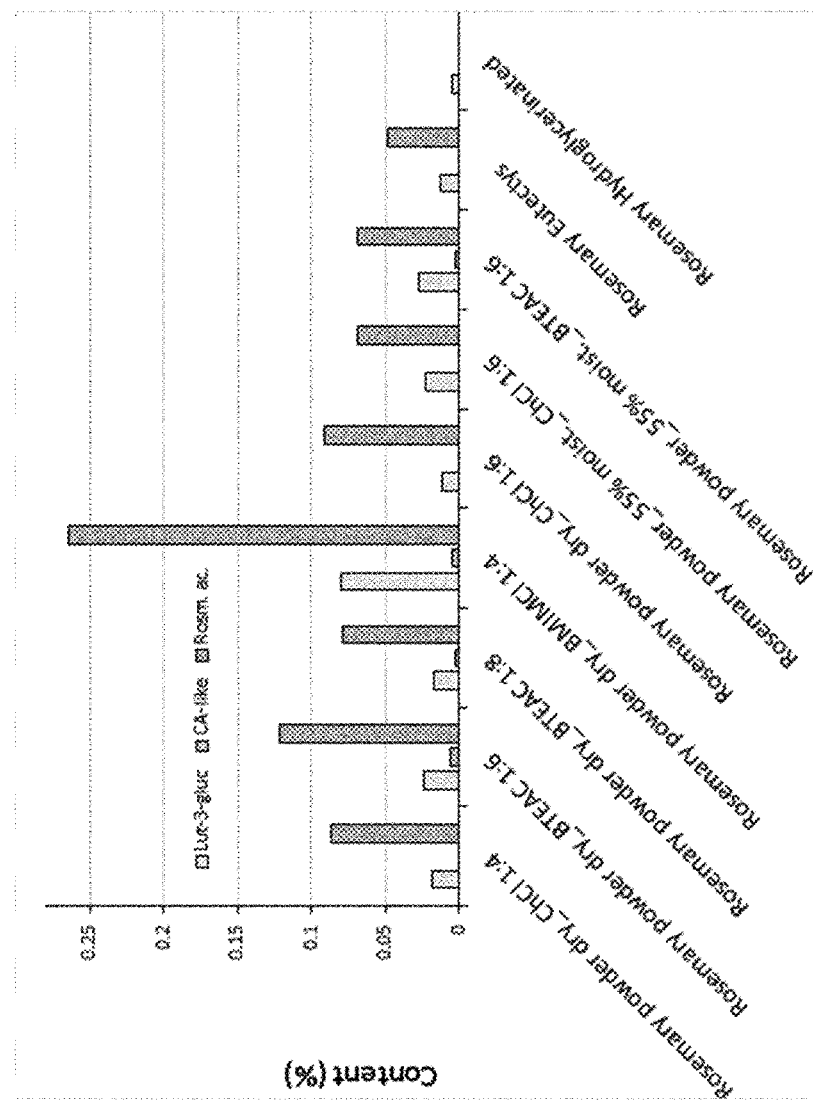
FIG. 2: Content of selected antioxidants extracted from dried rosemary biomass with pure amines compared with Eutectys and hydroglycerinated extractants, measured by H PLC.

FIG. 2 shows the content in some important phytoactives extracted from dried rosemary leaves such as luteoline-3-glucuronide, rosmarinic acid and carnosic acid. The data presented here also contain the values corresponding to rosemary extracts obtained with (i) already formed DES used as extraction solvent (Rosemary Eutectys™) and (ii) already formed hydroglycerinated solvent (Rosemary hydroglycerinated).

Example 3A3: Dried Rosemary Leaves (*Rosmarinus officinalis* L.)+55% Weight $H_2O$+Amines Example 3A3 shows a typical mixture of dried rosemary powder first added with 55% weight of $H_2O$ then added with amine in various stoichiometric ratios.

The value of 55% water was chosen as it typically corresponds to the difference observed between fresh and dried rosemary leaves. The mixture was left in an open vessel for three days after vigorous mixing via mechanic stirring. The addition of $H_2O$ is to increase the rate of extraction by decreasing the viscosity of the amine, hence improving the mass transport. This would naturally occur in an open system due to the hygroscopic nature of the amines used, however, this would reduce the time taken to reach equilibrium.

The optimum weight ratio range of dried rosemary leaves:amine was found to be between 1:1 and 1:10. Example 3A3 is the result of combining 0.5 g of dried rosemary leave powder, 2.0 g of ChCl and 0.275 g of $H_2O$ added prior to the amine addition (weight ratio: 1:4:0.55, resp.).

Other eutectic extracts were obtained from dried rosemary powder and ChCl (1:6) or BTEAC (1:6). These latter two systems have been assessed for their antioxidant activity (Table 3) and their content in rosmarinic acid, carnosic acid and luteoline-3-glucuronide (FIG. 2).

*Choisya* leaves with 4.5 g of ChCl (weight ratio: 1:6, resp.) and example A4 (b) is the result of mixing 0.75 g of fresh *Choisya* leaves with 4.5 g of BTEAC (weight ratio: 1:4:2, resp.). In both cases the resulting liquid was centrifuged and filtered. When ChCl was used as amine, a brown liquid was obtained, while a green liquid was produced with BTEAC.

ORAC and CAT value measurements of these mixture showed good content of antioxidant material within the extract.

Figure 3:
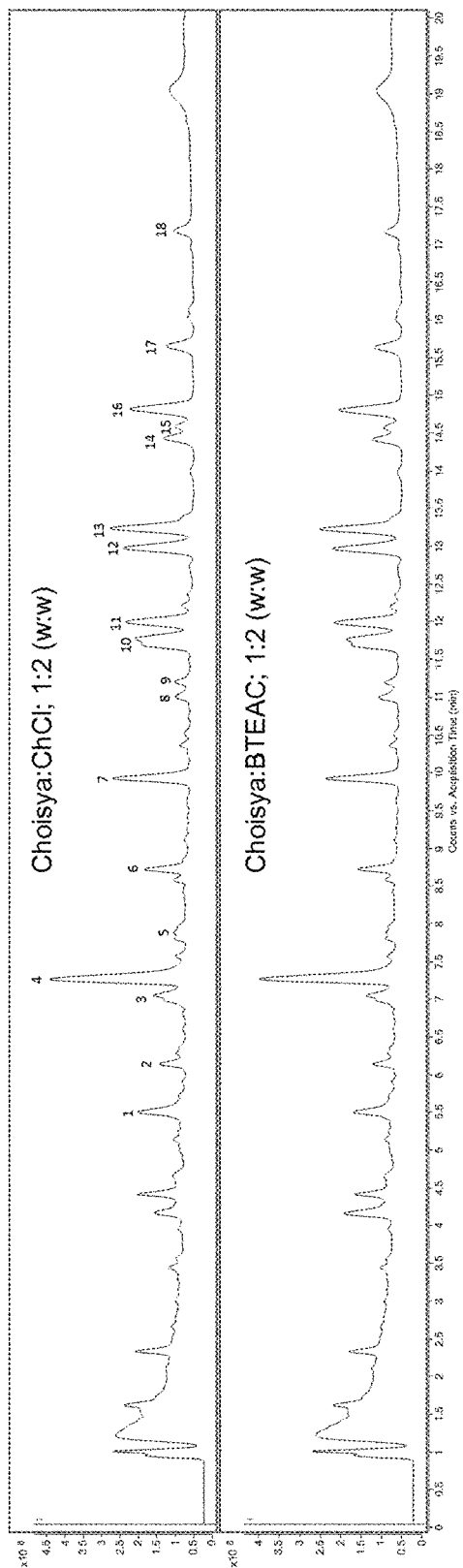
FIG. 3. LC-MS chromatogram (ESI-TIC) of the *Choisya* eutectic extracts obtained through eutectigenesis-assisted extraction of *Choisya* leaves by ChCl (1:2) and BTEAC (1:2).

In this example (FIG. 3), no significant difference can be observed in the LC-MS profiles of eutectic extracts obtained using an aliphatic (ChCl) or an aromatic (BTEAC) amine salt.

TABLE 3

Compositions and antioxidant activities of different eutectic extracts.

| Nat. product Material | Added amine | Added water | Nat. prod.:amine:water weight ratio | Eutectic formation | ORAC value (μmol TE/g) | CAT value (μmol TE/g) |
|---|---|---|---|---|---|---|
| Dried rosemary | ChCl | 55% (w) | 1:6:0.55 | Melt | 43.7 | 4.5 |
| Dried rosemary | BTEAC | 55% (w) | 1:6:0.55 | Melt | 100.4 | 26.8 |

Example 3A4: Fresh *Choisya* Leaves (*Choisya ternata*)+Amines

The extraction of phenolic compounds and other active compounds such as alkaloids can also take place from other leaves such as *Choisya* (*Choisya ternata*) belonging to the Rutaceae family.

Figure 4:
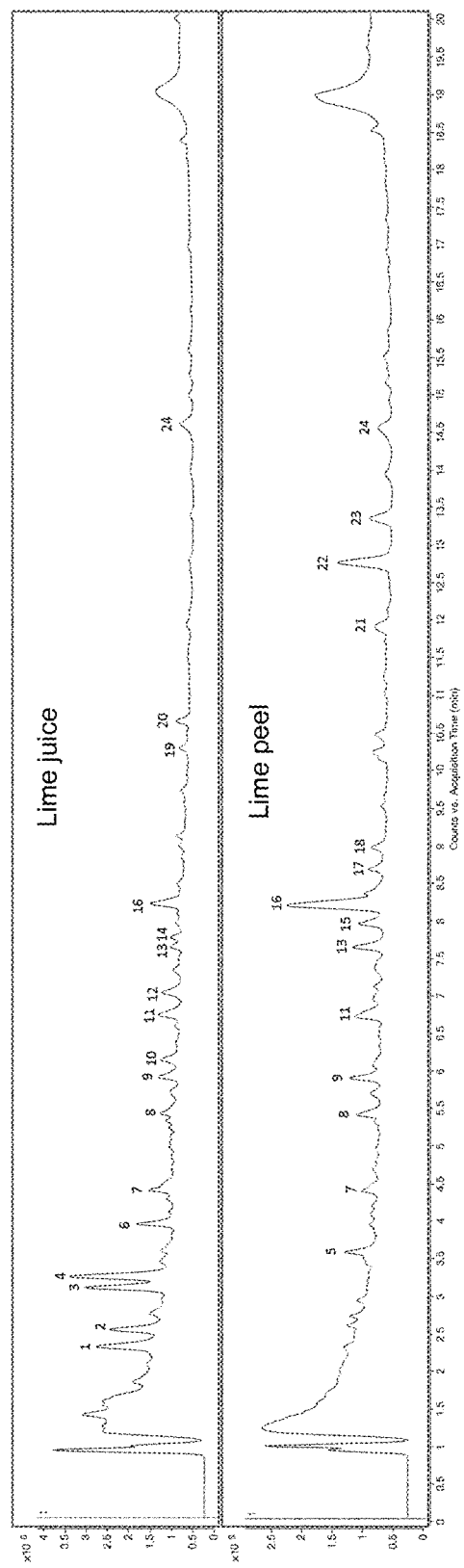
FIG. 4. LC-MS chromatogram of the lime eutectic extract obtained through solid-state extraction of rind and juice of lime by ChCl.

The same trends are observed in extract efficiency with amine amount and type. Fresh *Choisya* leaves were mixed together with amines in a pestle and mortar and left in an open vessel for seven days. The optimum ratio range of fresh *Choisya*:amine was found to be between 1:1 and 1:10. Example A4 (a) is the result of mixing 0.75 g of fresh Moreover, LC-MS data show that the extracted compounds from *Choisya* leaves are mainly phenolics such as flavonoids (e.g. apigenin-diglucoside, rutin, luteolin-7-rutinoside), phenolic acid derivatives (rosmarinic acid glucoside), and alkaloids (quinoline alkaloid and its numerous isomers, scopolamine, balfourodine, evoxine, methylevoxine, and choisyne to only cite a few examples) (FIG. 4). They mostly contain HBD moieties that can give a H-bond to the tested amine salt, either ChCl or BTEAC (Table 4).

TABLE 4

MS identification of compounds from choisya eutectic extracts.

| Peak | Identification | Formula found | $[M + H]^+$ | Fragment ion | Δ +/− | HBD moiety | HBA moiety | Aromatics (homo/hetero) | Bp (° C.)[h] | LogP[i] |
|---|---|---|---|---|---|---|---|---|---|---|
| 1 | Apigenin 6,8-di-C-glucoside | $C_{27}H_{30}O_{15}$ | 595.1662 | — | 0.95 | 11 | 15 | 2/0 | 974 | −2.621 |
| 2 | Quinoline alkaloid 1[a] | $C_{16}H_{19}NO_3$ | 274.1438 | — | −0.22 | | | | | |
| 3 | Rutin | $C_{27}H_{30}O_{16}$ | 611.1607 | 465.1036/ 303.0507 | −0.07 | 10 | 16 | 2/0 | 983 | −0.903 |
| | Scopolamine | $C_{17}H_{21}NO_4$ | 304.1548 | — | −1.39 | 1 | 5 | 1/0 | 460 | 0.693 |
| 5 | Rosmarinic acid β-D-glucoside | $C_{24}H_{26}O_{13}$ | 523.1448 | 361.0929 | 1.05 | 8 | 13 | 2/0 | 876 | −1.411 |
| 5' | Luteolin 7-O-rutinoside | $C_{27}H_{30}O_{15}$ | 595.1662 | 287.0558 | −1.21 | 9 | 15 | 2/0 | 954 | 0.180 |
| 6 | Balfourodine | $C_{16}H_{19}NO_4$ | 290.1388 | — | −0.62 | 1 | 5 | 1/0 | 436 | −0.174 |
| 7 | Evoxine | $C_{18}H_{21}NO_6$ | 348.1448 | — | −1.92 | 2 | 7 | 1/1 | 546 | 1.718 |
| 8 | Quinoline alkaloid 2[b] | $C_{18}H_{21}NO_5$ | 332.1496 | — | −1.68 | | | | | |
| 9 | Methylevoxine | $C_{19}H_{23}NO_6$ | 362.1595 | — | 0.45 | 1 | 7 | 1/1 | 525 | 2.151 |
| 10 | Skimmianine | $C_{14}H_{13}NO_4$ | 260.0921 | — | −1.65 | 0 | 5 | 1/1 | 402 | 2.178 |
| 10' | Choisyine | $C_{18}H_{19}NO_5$ | 330.1338 | — | −0.72 | 1 | 6 | 1/1 | 508 | 2.036 |
| 11 | Kokusaginine | $C_{14}H_{13}NO_4$ | 260.0924 | — | −3.7 | 0 | 5 | 1/1 | 402 | 2.178 |
| 11' | Quinoline alkaloid 3[c] | $C_{17}H_{17}NO_4$ | 300.1244 | — | −5.79 | nd | nd | nd | nd | nd |
| 12 | Quinoline alkaloid 4[d] | $C_{18}H_{19}NO_4$ | 314.1390 | — | −1.33 | nd | nd | nd | nd | nd |
| 13 | Quinoline alkaloid 5[e] | $C_{18}H_{20}NO_5$ | 330.1337 | — | −0.62 | nd | nd | nd | nd | nd |
| 14 | Quinoline alkaloid 6[f] | $C_{18}H_{19}NO_4$ | 314.1393 | — | −2.11 | nd | nd | nd | nd | nd |
| 15 | Quinoline alkaloid 7[g] | $C_{19}H_{21}NO_5$ | 344.1510 | — | −4.92 | nd | nd | nd | nd | nd |
| 16 | Choisyine isomer | $C_{18}H_{19}NO_5$ | 330.1337 | — | −2.16 | 1 | 6 | 1/1 | 508 | 2.036 |

[a]Daurine (or forthucine)
[b]Dihydroepimacronine (or Tazettine or Unsevine)
[c]2-[(2R)-10-Methoxy-1,2-dihydrodifuro[2,3-b:3',2'-f]quinolin-2-yl]-2-propanol
[d]and[f] (3E)-4-(4,6-Dimethoxyfuro[2,3-b]quinolin-5-yl)-2-methyl-3-buten-2-ol
[e](2R)-3-Chloro-1-[(4,8-dimethoxyfuro[2,3-b]quinolin-7-yl)oxy]-3-methyl-2-butanol
[g]3-Methyl-1-(4,6,7-trimethoxyfuro[2,3-b]quinolin-5-yl)-3-buten-2-ol Furthermore, ORAC and CAT value measurements of these eutectic mixtures showed significant antioxidant activities for crude liquid extracts (Table 5), which is corroborated by the LC-MS identification of four potent antioxidant molecules: rutin, luteolin 7-O-rutinoside, apigenin 6,8-di-C-glucoside, and rosmarinic acid β-D-glucoside (Table 4).

TABLE 5

Compositions and antioxidant activities of different eutectic extracts.

| Natural Product Material | Added amine | Nat. product:amine weight ratio | Eutectic formation | ORAC value (μmol TE/g) | CAT value (μmol TE/g) |
|---|---|---|---|---|---|
| Fresh *choisya* | ChCl | 1:4 | Melt | 31.7 | 4.9 |
| Fresh *choisya* | ChCl | 1:6 | Melt | 23.9 | 5.1 |
| Fresh *choisya* | ChCl | 1:8 | Melt | 18.1 | 3.1 |
| Fresh *choisya* | ChCl | 1:8 (repetition) | Melt | 21.2 | 5.2 |
| Fresh *choisya* | BTEAC | 1.4 | Melt | 30.0 | 4.5 |
| Fresh *choisya* | BTEAC | 1:4 (repetition) | Melt | 37.3 | 8.0 |

None of the identified alkaloids bear reducing group, such as a phenolic moiety, capable of antioxidant potential. However, they are endowed with a broad range of biological activities. One can cite scopolamine which has as a number of uses in medicine, where it is used to treat postoperative nausea and vomiting and sea sickness, leading to its use by scuba divers. It is also used in the treatment of motion sickness, gastrointestinal spasms, renal or biliary spasms, bowel colic, irritable bowel syndrome, clozapine-induced hypersalivation (drooling), and eye inflammation.

Examples 3A5 and 3A6: Dried Blueberry Juice (*Cyanococcus*)+Amines

Examples 3A5 and 3A6 show ChCl mixed with dried blueberry juice powder using both thermal evaporation (example A5) and freeze drying (example A6) and to produce a white powder. Upon addition of the components (amines+dried blueberry juice), mixing occurred by using a pestle and mortar.

The mixture was left in an open vessel at room temperature for seven days. A very pale yellow/brown liquid was formed. This was the same for all amines tried (ChCl/BTEAC/BmimCl).

The weight ratio of amines to natural product did not alter the colour of the liquid. The optimum natural product:amine ratio for this system was found to be between 1:2 and 1:8. Example A5 is the result of mixing 0.5 g of thermally evaporated (heat-dried) blueberry juice with 2.0 g of ChCl (weight ratio: 1:4, resp.) and example A6 is the result of mixing 0.5 g of freeze dried blueberry juice with 2.0 g of ChCl (weight ratio: 1:4, resp.).

Other eutectic extracts were obtained from dried blueberry juice either in its heat-dried or freeze-dried form (Table 6). Some melt were obtained with a different weight ratio with ChCl (1:2, 1:6), while others were found with BTEAC (1:4, 1:8) and BmimCl (1:4).

TABLE 6

Compositions and antioxidant activities of different eutectic extracts.

| Natural Product Material | Juice drying technique | Added amine | Nat. prod.:amine weight ratio | Eutectic formation | ORAC value (μmol TE/g) | CAT value (μmol TE/g) |
|---|---|---|---|---|---|---|
| Blueberry juice | Heat-dried | ChCl | 1:4 | Melt | 9.6 | 3.7 |
| Blueberry juice | Heat-dried | ChCl | 1:4 (repetition) | Melt | 9.0 | 2.9 |
| Blueberry juice | Heat-dried | BTEAC | 1:4 | Melt | 6.6 | 2.2 |
| Blueberry juice | Freeze-dried | ChCl | 1:2 | Melt | 17.5 | 6.4 |
| Blueberry juice | Freeze-dried | ChCl | 1:4 | Melt | 12 | 2.8 |
| Blueberry juice | Freeze-dried | ChCl | 1:6 | Melt | 10.7 | 4.0 |
| Blueberry juice | Freeze-dried | BTEAC | 1:4 | Melt | 11.9 | 4.6 |
| Blueberry juice | Freeze-dried | BTEAC | 1:8 | Melt | 7.9 | 2.8 |
| Blueberry juice | Freeze-dried | BmimCl | 1:4 | Melt | 13.8 | 5.7 |

Example 3A7: Dried Blueberry Pulp (*Cyanococcus*)+Amines

Example 3A7 is the result of mixing 0.5 g of dried blueberry pulp with 4.0 g of ChCl (weight ratio: 1:4, resp.) with a pestle and mortar and left in an open vessel for seven days.

The optimum natural product:amine weight ratio for this system was found to be between 1:2 and 1:8 as other eutectic melts were obtained using BTEAC at a weight ratio of 1:4 and 1:8.

The resulting liquid extract is darker in colour than the resulting extracts from the dried blueberry juice tests. This was the same for all amines tried with the pulp and the ratio of natural product:amine did not alter the colour of the liquid. In terms of antioxidant activity, we can observe a slight decrease of the activity when the amine proportion is increased which is probably due to a sort of dilution effect of the antioxidant molecules in the amine (Table 7).

TABLE 7

Compositions and antioxidant activities of different eutectic extracts.

| Natural Product Material | Added amine | Natural Product:amine weight ratio | Eutectic formation | ORAC value (μmol TE/g) | CAT value (μmol TE/g) |
|---|---|---|---|---|---|
| Blueberry skin | ChCl | 1:8 | Melt | 10.9 | 4.2 |
| Blueberry skin | BTEAC | 1:2 | Melt | 16.5 | 6.2 |
| Blueberry skin | BTEAC | 1:8 | Melt | 13.9 | 6.1 |

Examples 3A8, 3A9, 3A10, 3A11: *Capsicum* (*Capsicum annuum*)/Green Chilli (*Capsicum frutescens*)+Amines The hulls and seeds of *Capsicum* and green chilli fruits were separately mixed with amines to recover the natural substances (able to donate hydrogen bonds) contained in these parts of the plants.

Example 3A8 (a) shows the result of 0.5 g of fresh *Capsicum* hull mixed with 3.0 g of ChCl (ratio: 1:6) and example 3A10 (a) shows the result of combining 0.5 g of fresh green chilli hull with 4.0 g of ChCl (ratio: 1:8). Example 3A8 (b) shows the result of 0.5 g of fresh *Capsicum* hull mixed with 3.0 g of BTEAC (ratio: 1:6) and example 3A10 (b) shows the result of 0.5 g of fresh green chilli hull mixed with 4.0 g of BTEAC (ratio: 1:8).

The colour of the eutectic extract varies depending on the amine used. When ChCl is used (examples 3A8 (a) and 3A10 (a)) a very lightly yellow coloured solution is formed, however when BTEAC (examples 3A8 (b) and 3A10 (b)) is used, a pink solution is formed.

Example 3A9 shows the result of 0.5 g of ground *Capsicum* seeds with 4.0 g ChCl (ratio: 1:8) and example 3A11 shows the result of 0.5 g of ground green chilli seeds with 4.0 g of ChCl (ratio: 1:8).

Other ratios were also found to lead to the formation of eutectic melts (Table 8). In all examples the pure amine was mixed with the plant material using a pestle and mortar and left in an open vessel for seven days at room temperature. The resulting liquid was centrifuged and filtered. The optimum weight ratio range of *Capsicum*:amine or green chilli:amine was found to be between 1:2 and 1:10.

TABLE 8

Compositions and antioxidant activities of different eutectic extracts.

| Natural Product Material | Added amine | Nat product:amine weight ratio | Eutectic formation | ORAC value ($\mu$mol TE/g) | CAT value ($\mu$mol TE/g) |
| --- | --- | --- | --- | --- | --- |
| *Capsicum* skin | ChCl | 1:4 | Melt | 3.9 | 2.2 |
| *Capsicum* skin | ChCl | 1:6 | Melt | 10.5 | 3.4 |
| *Capsicum* skin | BTEAC | 1:2 | Melt | 2.6 | 0.5 |
| *Capsicum* skin | BTEAC | 1:2 (repetition) | Melt | 3.5 | 0.6 |
| *Capsicum* skin | BTEAC | 1:4 | Melt | 2.1 | 0.5 |
| *Capsicum* seed | ChCl | 1:4 | Melt | 3.8 | 1.3 |
| *Capsicum* seed | ChCl | 1:8 | Melt | 4.4 | 1.1 |
| Green chilli skin | ChCl | 1:2 | Melt | 13.9 | 3.9 |
| Green chilli skin | ChCl | 1:8 | Melt | 7.2 | 1.3 |
| Green chilli skin | ChCl | 1:8 (repetition) | Melt | 5.9 | 1.7 |
| Green chilli skin | BTEAC | 1:4 | Melt | 11 | 1.8 |
| Green chilli skin | BTEAC | 1:8 | Melt | 12.6 | 2.4 |
| Green chilli skin | BTEAC | 1:8 (repetition) | Melt | 10.8 | 2.7 |
| Green chilli seed | ChCl | 1:8 | Melt | 3.9 | 0.7 |
| Green chilli seed | ChCl | 1:8 (repetition) | Melt | 3.1 | 0.9 |

Example 3A12: Dried Aubergine (*Solanum melongena*)+Amines

Example 3A12 shows the results of mixing 0.5 g of dried aubergine juice with 2.0 g of ChCl and had been left in an open vessel for seven days (weight ratio: 1:4, resp.). The liquid was centrifuged and filtered. A light yellow coloured liquid resulted and did not vary in colour when alternative amines were used. The flesh of an aubergine was juiced and freeze-dried. The resulting dried pulp was then ground into a powder. The optimum weight ratio range of aubergine:amine was found to be between 1:2 and 1:8. Example A12 shows the resulting liquid eutectic extract using ChCl as the amine. Table 9 also exemplifies the possibility to use BTEAC to form a eutectic melt.

TABLE 9

Compositions and antioxidant activities of different eutectic extracts.

| Natural Product Material | Added amine | Natural Product:amine weight ratio | Eutectic formation | ORAC value ($\mu$mol TE/g) | CAT value ($\mu$mol TE/g) |
| --- | --- | --- | --- | --- | --- |
| Freeze Dried Aubergine flesh | ChCl | 1:4 | Melt | 4.7 | 0.2 |
| Freeze Dried Aubergine flesh | BTEAC | 1:4 | Melt | 15.9 | 3.1 |

Example 3A13: Ginger (*Zingiber officinale*)+Amines

Example 3A13 shows how a root, in this case whole ginger root could be extracted with an amine. The ginger was juiced, freeze dried and ground into a powder before addition of the amine. Example 3A13 demonstrates the end result of mixing 0.5 g of dried ginger with 2.0 g of ChCl (weight ratio: 1:4, resp.) using a pestle and mortar and leaving in an open vessel for seven days. This eutectic extract was centrifuged and filtered in the same manner as other samples.

The optimum ratio range in which dried ginger could be extracted from was found to be 1:2 to 1:8 ginger:amine as other ratios and amines (BTEAC) also yield eutectic melts.

TABLE 10

Compositions and antioxidant activities of different eutectic extracts.

| Natural Product Material | Added amine | Natural Product:amine weight ratio | Eutectic formation | ORAC value ($\mu$mol TE/g) | CAT value ($\mu$mol TE/g) |
| --- | --- | --- | --- | --- | --- |
| Ginger | ChCl | 1:2 | Melt | 4.6 | 1.9 |
| Ginger | ChCl | 1:4 | Melt | 6.1 | 1.7 |
| Ginger | BTEAC | 1:2 | Melt | 5.2 | 2.5 |
| Ginger | BTEAC | 1:4 | Melt | 7.4 | 1.6 |

Examples 3A14 and 3A15: Lime (*Citrus aurantifolia*)+Amines

The rind and juice of a lime, once separated from the flesh of the lime, have been mixed with various amines independently and have been shown to yield a eutectic extract with a high concentration of malic, citric and ascorbic acids. The rind was frozen with liquid $N_2$ and then ground into a powder prior to addition of amines and the juice was freeze dried.

To remove any insoluble solid material from the liquid phase, the mixture was centrifuged and then decanted. Example A14 is the result of mixing 0.5 g of dried and powdered lime rind with 3.0 g of ChCl (weight ratio: 1:6, resp.) and example A15 is the result of mixing 0.5 g of freeze dried lime juice with 3.0 g of ChCl (weight ratio: 1:6, resp.). Both samples were mixed using a pestle and mortar and left in an open vessel for ten days. The optimum lime:amine weight ratio to obtain a eutectic melt was found to range from 1:2 to 1:10 (Table 11).

TABLE 11

Compositions of two eutectic extracts from Lime.

| Natural Product Material | Added amine | Natural Product:amine weight ratio | Eutectic formation |
|---|---|---|---|
| Dried lime rind | ChCl | 1:6 | Melt |
| Freeze-dried lime juice | ChCl | 1:6 | Melt |

TABLE 12

MS identification of compounds from lime eutectic extracts.

| Peak | Possible identification | Formula found | [M + H]$^+$ | Fragment ion | Δ ppm +/− | HBD moiety | HBA moiety | Aromatics (homo/hetero) | Mp (° C.)$^h$ | Bp (° C.)$^i$ | LogP$^j$ |
|---|---|---|---|---|---|---|---|---|---|---|---|
| 1 | Cinamic acid | $C_9H_8O_2$ | 149.0598 | — | −2.97 | 1 | 2 | 1/0 | — | 300 | 1.212 |
| 3 | Dimethyl citrate | $C_8H_{12}O_7$ | 221.0665 | 203.0551/ 185.0445 | 2.85 | 2 | 7 | 0 | — | 405 | 0.244 |
| 4 | Dimethyl citrate isomer | $C_8H_{12}O_7$ | 221.0665 | — | | 2 | 7 | 0 | — | 405 | 0.244 |
| 8 | Apigenin 6,8-di-C-glucoside | $C_{27}H_{30}O_{15}$ | 595.1659 | — | −0.39 | 11 | 15 | 2/0 | — | 974 | −2.621 |
| 9 | Diosmetin 6,8-di-C-glucoside | $C_{28}H_{32}O_{16}$ | 625.1765 | — | −0.73 | 11 | 16 | 2/0 | — | 986 | −1.871 |
| 11 | Eriocitrin (eriodictyol 7-O-rutinoside) | $C_{27}H_{32}O_{15}$ | 597.1815 | 435.1301/ 289.0715 | −0.51 | 9 | 15 | 2/0 | 160 | 957 | −1.813 |
| 12 | Rutin | $C_{27}H_{30}O_{16}$ | 611.1628 | 465.1058/ 303.0513 | −4.01 | 10 | 16 | 2/0 | — | 983 | −0.903 |
| 12 | Limonin | $C_{26}H_{30}O_8$ | 471.2021 | — | −1.69 | 0 | 8 | 0/1 | 298 | 668 | 0.474 |
| 13 | Narirutin (Naringenin 7-O-rutinoside) | $C_{27}H_{32}O_{14}$ | 581.1871 | 435.1305/ 273.0766 | −2.21 | 8 | 14 | 2/0 | 180 | 924 | −0.522 |
| 13' | Diosmetin 8-C-glucoside | $C_{22}H_{22}O_{11}$ | 463.0124 | — | −1.2 | 7 | 11 | 2/0 | — | 784 | 0.736 |
| 13" | Natsudaidain | $C_{21}H_{22}O_9$ | 419.1345 | — | −4.08 | 1 | 9 | 2/0 | 156 | 608 | 2.124 |
| 14 | Eriodictyol C-glucoside | $C_{21}H_{22}O_{11}$ | 451.1217 | — | 4.76 | 8 | 11 | 2/0 | — | — | — |
| 15 | Rhoifolin (or sorhoifolin)$^a$ | $C_{27}H_{30}O_{14}$ | 579.1715 | — | −1.24 | 8 | 14 | 2/0 | 260 | 916 | −0.062 |
| 16 | Hesperidin | $C_{28}H_{34}O_{15}$ | 611.1972 | 449.1448/ 303.0870 | −0.31 | 8 | 15 | 2/0 | 262 | 930 | −1.212 |
| 17 | Scutellarein 7,4-dimethylether sophoroside | $C_{29}H_{32}O_{17}$ | 653.1712 | — | −0.47 | 8 | 17 | 2/0 | — | — | — |
| 18 | Nomilin glucoside | $C_{34}H_{46}O_{15}$ | 694.7274 | — | −0.42 | 5 | 15 | 0/1 | — | 852 | 0.524 |
| 19 | Poncirin$^b$ (or its isomers: neoponcirin or didymin) | $C_{34}H_{28}O_{14}$ | 595.2035 | — | −1.29 | 7 | 14 | 2/0 | 210 | 900 | 0.537 |
| 19' | Limonexin | $C_{26}H_{30}O_{10}$ | 503.1918 | — | −2.60 | 1 | 10 | 0 | — | 784 | −2.915 |
| 21 | Citrobilin | $C_{28}H_{34}O_{11}$ | 564.2469 | — | −1.57 | 1 | 11 | 0 | — | 725 | −1.550 |
| 21' | Hesperetin glucoside | $C_{22}H_{24}O_{11}$ | 464.2645 | — | −5.34 | 6 | 11 | 2/0 | — | — | — |
| 22 | Citropten | $C_{11}H_{10}O_4$ | 207.0651 | — | 0.26 | 0 | 4 | 1/1 | 149 | 388 | 1.891 |
| 23 | Bergapten | $C_{12}H_8O_4$ | 217.0499 | — | −2.07 | 0 | 4 | 1/2 | 188 | 412 | 2.035 |
| 23' | Isopimpinellin | $C_{13}H_{10}O_5$ | 247.0604 | — | −1.74 | 0 | 5 | 1/2 | 151 | 449 | 1.407 |
| 24 | Limonin isomer | $C_{26}H_{30}O_8$ | 471.2023 | — | −2.06 | 0 | 8 | 0/1 | — | — | — |
| 24' | Geranyl propionate | $C_{13}H_{22}O_2$ | 211.1692 | — | −1.04 | 0 | 2 | 0 | — | — | — |

Table 12 gives the chemical compounds founds and identified by LC-MS in ESI+ for the two eutectic extracts. First, it appears that the chemical profile of lime juice eutectic extract is different from that obtained from the rind part. Among other differences, one can note the higher concentration of hesperidin in lime peel compared to the juice, as well as the higher contents of citrobilin (triterpenoid), citropten (a coumarin currently found in lime essential oils), and bergapten (a furocoumarin also currently found in citrus essential oils). Table 13 provides quantitation of the compounds found in eutectic extracts of lime peel and juice.

TABLE 13

Quantitation of compounds from lime peel and juice eutectic extracts

| Compounds | Lime juice ppm | Lime peel ppm |
|---|---|---|
| Apigenin 6,8-di-glucoside [1] | 88.9 | 157.1 |
| Diosmetin 6,8-di-glucoside [1] | 84.8 | 35.95 |
| Eriocitrin [2] | 144.3 | 202.15 |
| Rutin [1] | 25.45 | 0 |
| Narirutin [2] | 37.77 | 66.93 |
| Eriodyctiol C-glucoside [1] | 7.4 | 35.9 |
| Rhoifolin [1] | 21.15 | 166.25 |
| Hesperidin [2] | 171.8 | 1442.5 |
| Scutellarein dimethylether sophoroside [1] | 0 | 41.9 |
| Nomilin glucoside [3] | 0 | 246.43 |
| Poncirin [4] | 3.75 | 2.31 |
| Furanocoumarin [4] | 0 | 3.67 |
| Citropten [4] | 0.57 | 21.06 |
| Bergapten & isopimpinellin [4] | 0.56 | 9.16 |

[1] Expressed as rutin
[2] Expressed as hesperidin
[3] Expressed as nomilin
[4] Expressed as coumarin Example 3A16: *Cedrus* Bark (*Cedrus* Spp.)+Amines Example 3A16 shows that a bark can be extracted using the same eutectigenesis-assisted extraction process to yield an extract high in phytoactives. The sample shown in example 3A16 was the result of combining 0.5 g of *Cedrus* bark powder with 3.0 g of BmimCl (weight ratio: 1:6, resp.) using a pestle and mortar and leaving in an open vessel for eight days. *Cedrus* bark was frozen using liquid $N_2$ and then ground into a fine powder using a pestle and mortar.

Noteworthy, other weight ratios (1:8) and amines (BTEAC, BmimCl) allows obtaining eutectic melts (Table 14). The optimum weight ratio range of *Cedrus* bark to amine was found to be 1:2 to 1:10. The resulting extract was a deep brown colour and ORAC and CAT values showed relatively strong antioxidant properties demonstrating that antioxidant components had been recovered by the amine. *Cedrus* bark:BTEAC (1:8) followed by *Cedrus* bark:BmimCl (1:6) exhibited the highest activities we have found using the eutectigenesis-assisted extraction technique (without further purification): 302.9 and 285.2 µmol TE/g of liquid extract (ORAC values), respectively (Table 14). The highest CAT value (79.1 µmol TE/g) was also observed for the eutectic extract from *Cedrus* bark:BTEAC (1:8), though it was not from the same repetition.

TABLE 14

Compositions and antioxidant activities of different eutectic extracts from *Cedrus* bark.

| Natural Product Material | Added amine | Natural Product:amine weight ratio | Eutectic formation | ORAC value (µmol TE/g) | CAT value (µmol TE/g) |
|---|---|---|---|---|---|
| Powdered *Cedrus* bark | ChCl | 1:8 | Melt | 152.3 | 45.5 |
| Powdered *Cedrus* bark | BTEAC | 1:8 | Melt | 302.9 | 42.7 |
| Powdered *Cedrus* bark | BTEAC | 1:8 (repetition) | Melt | 258.2 | 79.1 |
| Powdered *Cedrus* bark | BmimCl | 1:6 | Melt | 285.2 | 37.0 |
| Powdered *Cedrus* bark | BmimCl | 1:8 | Melt | 170.5 | 35.2 |

Example 3A17: Java Tea, *Orthosiphon aristatus* (Blume) Miq. (Syn. *Orthosiphon stamineus* Benth.), aerial part (dry & milled)+amines Example 3A17 shows a typical extract of the herb *Orthosiphon* using pure amines. In this example, 0.5 g of dried *Orthosiphon* was mixed with 3.0 g ChCl (weight ratio: 1:6, resp.) and mixed together using a pestle and mortar. The mixture was then left for in an open vessel for eight days. The resulting liquid was a light brown/orange colour. Other ratios (1:4, 1:8) and another amine (BmimCl) were also found to yield eutectic melts (Table 15). The optimum weight ratio range of *Orthosiphon*:amine was found to be between 1:2 to 1:8. The ORAC and CAT values shows that antioxidant compounds are present in this liquid extract, with relatively high antioxidant activities for the eutectic extract coming from *Orthosiphon*:BmimCl (1:4): 133.1 (ORAC) and 40.9 (CAT) µmol TE/g.

TABLE 15

Compositions and antioxidant activities of different eutectic extracts from *Orthosiphon*.

| Natural Product Material | Added amine | Natural Product:amine weight ratio | Eutectic formation | ORAC value (µmol TE/g) | CAT value (µmol TE/g) |
|---|---|---|---|---|---|
| *Orthosiphon* herb | ChCl | 1:6 | Melt | 44.5 | 12.6 |
| *Orthosiphon* herb | ChCl | 1:8 | Melt | 28.6 | 7.3 |
| *Orthosiphon* herb | BmimCl | 1:4 | Melt | 133.1 | 40.9 |
| *Orthosiphon* herb | BmimCl | 1:8 | Melt | 51.4 | 15.1 |

Example 3A18: Ziziphus (*Ziziphus jujuba* Mill., Seed (Dry & Milled))+Amines

Example 3A18 shows a typical extract of the seeds from the *Ziziphus* plant (jujube). In this example, 0.5 g of dried *Ziziphus* seed was mixed with 3.0 g ChCl (weight ratio: 1:6, resp.) and mixed using a pestle and mortar and left in an open vessel for seven days. Other ratios (1:4, 1:8) and amines (BTEAC, BmimCl) were also found to yield eutectic melts (Table 16). The optimum weight ratio range of *Ziziphus*:amine was found to be 1:2 to 1:8. The resulting liquid was a light brown/orange colour. Noteworthy, only BTEAC extract (ratio 1:6) gives a significant antioxidant activity in the ORAC method with a value of 41.4 µmol TE/g.

TABLE 16

Compositions and antioxidant activities of different eutectic extracts from *Ziziphus*.

| Natural Product Material | Added amine | Natural Product:amine weight ratio | Eutectic formation | ORAC value (µmol TE/g) | CAT value (µmol TE/g) |
|---|---|---|---|---|---|
| *Ziziphus* seed | ChCl | 1:6 | Melt | 4.3 | 2.7 |
| *Ziziphus* seed | ChCl | 1:8 | Melt | 3.7 | 1.7 |
| *Ziziphus* seed | BmimCl | 1:4 | Melt | 9.7 | 3.1 |
| *Ziziphus* seed | BmimCl | 1:8 | Melt | 4.5 | 1.7 |
| *Ziziphus* seed | BTEAC | 1:6 | Melt | 41.4 | 3.6 |

Example 3A19: Cilantro (*Coriandrum sativum* L., Leaf (Dry & Grinded))+Amines

Example 3A19 shows the resulting extract when 0.5 g of the herb cilantro (or coriander) is mixed with 2.0 g of ChCl (weight ratio: 1:4, resp.). The plant material was dried and powdered when mixed with different amines and left in an open vessel for ten days. Other ratios (1:6, 1:8) and another amine (BmimCl) were also found to yield eutectic melts (Table 17). The optimum weight ratio range of cilantro: amine was found to be 1:2 to 1:8. The resulting liquid was a light brown/orange colour.

TABLE 17

Compositions and antioxidant activities of different eutectic extracts from Cilantro.

| Natural Product Material | Added amine | Natural Product:amine weight ratio | Eutectic formation | ORAC value (µmol TE/g) | CAT value (µmol TE/g) |
|---|---|---|---|---|---|
| Cilantro leaves | ChCl | 1:6 | Melt | 9.7 | 3.6 |
| Cilantro leaves | ChCl | 1:8 | Melt | 5.6 | 2.1 |
| Cilantro leaves | BmimCl | 1:8 | Melt | 10.5 | 4.0 |

Examples 3B

Here are presented a set of results using various plant materials as bark, leaves, or seeds exemplifying the enhancement of the eutectic extract activity and profile using the purification process.

Example 3B1: *Cedrus* Bark Eutectic Extract Purification

Purification of the eutectic extract was carried out by liquid-liquid extraction using a long chain monounsaturated fatty acid as the immiscible phase. To 1.0 mL of the *Cedrus* bark eutectic extract, 0.75 mL of pure oleic acid was added and mixed via magnetic stirrer at 50° C. for 30 minutes. The resulting mixture was then centrifuged to maximise separation of the two layers. The upper layer was then isolated from the lower layer with a Pasteur pipette and both phases were evaluated in terms of antioxidant activity, BTEAC content and profiles of compounds absorbing at 280 nm (phenolics) and 350 nm (mostly flavonoids).

Both ORAC and CAT values increased by a factor >2 which represents a strong enhancement of the antioxidant activity (FIG. 4). This activity improvement following the purification step can be explained by a rise of compounds absorbing at 280 nm (mostly phenolics having antioxidant potential) and 350 nm (mostly flavonoid phenolics having antioxidant potential). Concomitantly, the content in BTEAC (amine devoid of any antioxidant activity) slightly decreases from 71 to 63% when the purification process is applied to the extract.

Example 3B2: Rosemary Leaf Eutectic Extract Purification

To 1.0 mL of the rosemary leaf eutectic extract, 0.5 or 0.75 mL of pure oleic acid was added and mixed via magnetic stirrer at 50° C. for 30 minutes. The resulting mixture was then centrifuged at 5000 rpm for 15 minutes to maximise separation of the two layers. The upper layer was then isolated from the lower layer.

Figure 5:
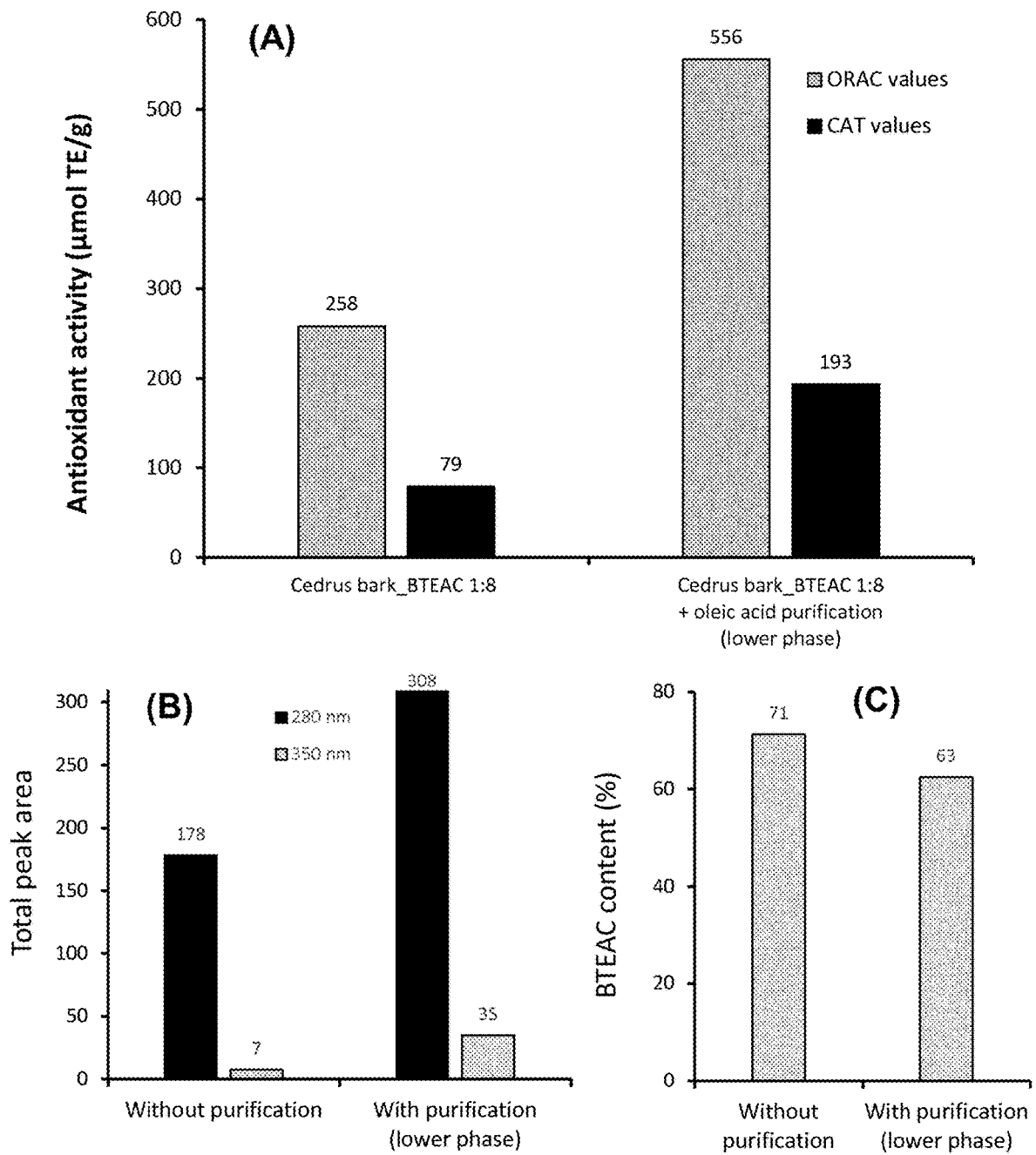
FIG. 5. Effect of the purification process of *Cedrus* bark eutectic extracts on their ORAC and CAT values (A), BTEAC content (B) and total peak area of compounds absorbing at 280 and 350 nm (C).

FIG. 5A shows an increase of the antioxidant activity of the rosemary eutectic extracts in both ORAC and CAT measurements following the application of the purification step. When 0.5 mL of pure oleic acid was used to wash 1 mL of liquid extract, the ORAC value of the resulting extract (lower layer) increased by 37% and the CAT value by 25%. Similarly, when using 0.75 mL oleic acid (for 1 mL extract), the ORAC value increased by 17.5% and CAT value by 19%.

This significant improvement of the activity is concomitant with an increase of two relatively hydrophilic phenolic antioxidants, namely rosmarinic acid and luteoline-3-O-glucuronide (FIG. 5B). Concurrently, the BTEAC and water are partially depleted from the extracts when the purification procedure is applied, although, as for *Cedrus* bark eutectic extract, the depletion remains modest (<10% for BTEAC; <20% for water). The BTEAC and the water removed from the extract are thus present in the upper layer of which they constitute a significant part (38-42%) almost equalling the proportion of oleic acid (43-46%) (FIG. 5C). Surprisingly, despite the immiscibility of water and oleic acid, the upper layers contain around 10% of water (FIG. 5C), which probably migrates as water H-bonded to BTEAC molecules (water-BTEAC complex).

Altogether, these results demonstrate that the purification step enables to raise the level of active molecules through a partial migration of non-antioxidant molecules into the phase formed by the long chain fatty acid, which consequently increases the activity that is considered. Noteworthy, this activity improvement can be obtained with other properties than just antioxidant properties.

In our experiments, no oleic acid migrates to the extracts during the purification step. Indeed, only low amounts of oleic acid (<1%) are found in the lower layer, whereas the non-purified rosemary eutectic extract already contain 1.7% oleic acid (FIG. 5C). It is also worth noting the slight antioxidant activity of the upper phase as measured by the ORAC method (FIG. 5A). First, compositional data shows that carnosic acid partially migrate from the extract into the washing phase (FIG. 5B). Second, it has been found that pure oleic acid can induce a positive value, although a modest one, for the ORAC method, unlike the CAT method.

Example 3B3: *Ziziphus* Seed Eutectic Extract Purification

To 1.0 mL of the *Ziziphus* seed eutectic extract, 0.75 mL of oleic acid was added and mixed via magnetic stirrer at 50° C. for 30 minutes. The resulting mixture was then centrifuged (5000 rpm for 15 mins) to maximise separation of the two layers. The upper layer was then isolated from the lower layer with a Pasteur pipette.

Figure 6:
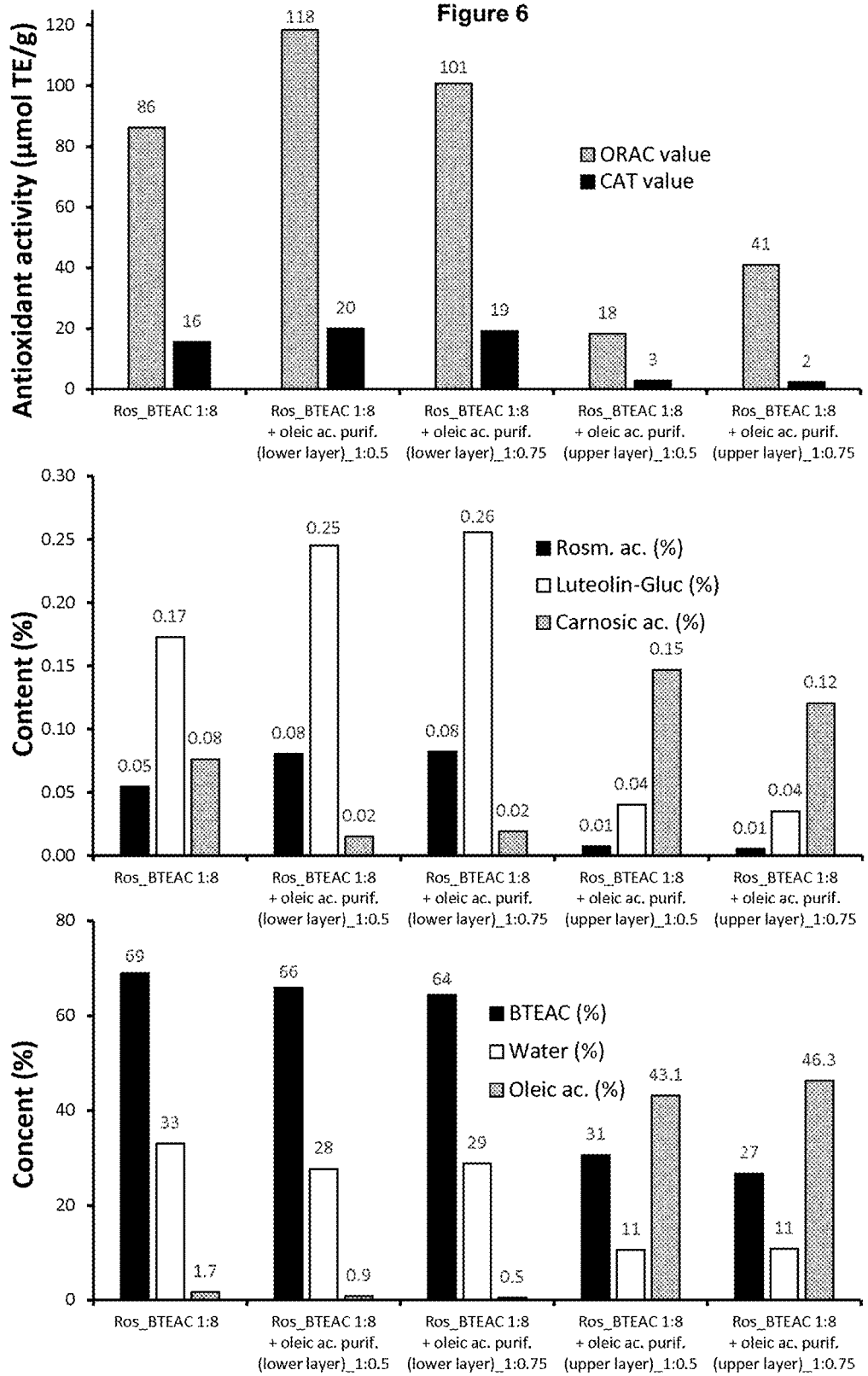
FIG. 6. Effect of the purification process of rosemary eutectic extracts on the ORAC and CAT values (A) and the content of some phenolics (B) and BTEAC, water and oleic acid (C).
Figure 7:
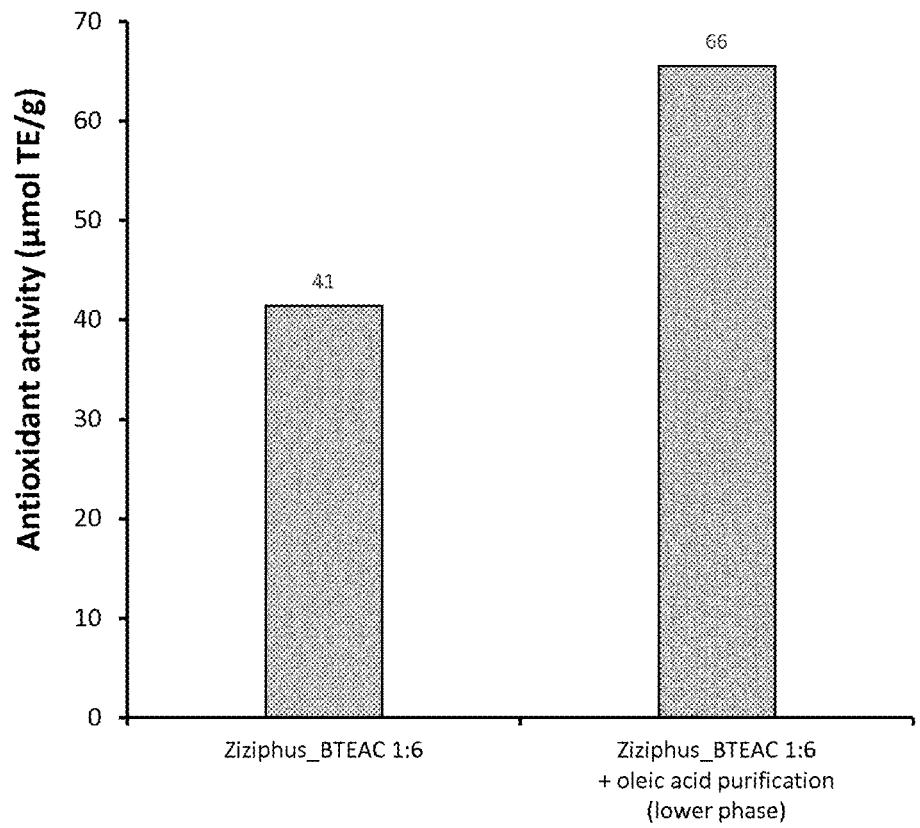
FIG. 7. Effect of the purification process on the ORAC values of *Ziziphus* eutectic extracts.

FIG. 6 shows that the purification technique leads to an increase of the ORAC activity of the eutectic extract of 61%. The parent extract contains around 67.5% of BTEAC before purification and 59.7% after purification, showing a partial depletion of the amine (13%). Consequently, the active molecules which are partitioned in the lower phase are concentrated, hence, probably, the increase of the antioxidant activity.

The invention claimed is:
1. A process for the purification of a eutectic extract or eutectic combination comprising:
   (i) mixing a eutectic extract or eutectic combination with a liquid that is immiscible in the eutectic extract or eutectic combination to form a mixture;
   (ii) allowing the mixture formed in step (i) to equilibrate into two phases; and
   (iii) separating the eutectic phase from the phase comprising the liquid that is immiscible in the eutectic extract or eutectic combination,
   wherein the liquid that is immiscible in the eutectic extract or eutectic combination is a lipid phase in a liquid form, a terpenic solvent, or an alcohol.
2. The purification process according to claim 1, wherein steps (i) to (iii) are repeated using the separated eutectic phase as the eutectic extract or eutectic combination in step (i) of the purification process.

3. The purification process according to claim 1, wherein the eutectic extract or eutectic combination may be prepared by
   (a) forming a mixture between at least one exogenous amine and biological material which is at least one of plant material, animal material, or prokaryotic biological material,
   (b) allowing the mixture to interact to form a liquid, gel or gel-like eutectic extract, and optionally, separating the liquid or gel/gel-like mixture from undissolved solids, or may be a eutectic extract or eutectic combination that has been previously prepared by extracting a biological material using a pre-prepared eutectic solvent.

4. The purification process according to claim 1, wherein the lipid phase in a liquid form is selected from free fatty acids, free fatty alcohol, triacylglycerols, and/or vegetable oil.

5. The purification process according to claim 1, wherein the terpene solvent is limonene or para-menthane.

6. The purification process according to claim 1, wherein the weight ratio of eutectic extract to immiscible liquid is from about 1:0.1 to about 1:10.

7. The purification process according to claim 1, wherein step (iii) separates the eutectic phase from the phase comprising the liquid that is immiscible in the eutectic extract by removing exogenous amine that has not formed a complex with the endogenous compounds in the biological material.

* * * * *